US009329182B2

(12) United States Patent
Burden

(10) Patent No.: US 9,329,182 B2
(45) Date of Patent: May 3, 2016

(54) METHOD OF TREATING MOTOR NEURON DISEASE WITH AN ANTIBODY THAT AGONIZES MUSK

(71) Applicant: Steven J. Burden, New York, NY (US)

(72) Inventor: Steven J. Burden, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/358,055

(22) PCT Filed: Nov. 14, 2012

(86) PCT No.: PCT/US2012/065023
§ 371 (c)(1),
(2) Date: May 14, 2014

(87) PCT Pub. No.: WO2013/074636
PCT Pub. Date: May 23, 2013

(65) Prior Publication Data
US 2015/0050289 A1 Feb. 19, 2015

Related U.S. Application Data

(60) Provisional application No. 61/693,857, filed on Aug. 28, 2012, provisional application No. 61/559,309, filed on Nov. 14, 2011.

(51) Int. Cl.
| | |
|---|---|
| *A61K 39/395* | (2006.01) |
| *A61P 21/00* | (2006.01) |
| *C07K 16/28* | (2006.01) |
| *G01N 33/573* | (2006.01) |
| *A61K 31/7088* | (2006.01) |
| *A61K 38/00* | (2006.01) |
| *C07K 14/705* | (2006.01) |

(52) U.S. Cl.
CPC .......... *G01N 33/573* (2013.01); *A61K 31/7088* (2013.01); *A61K 38/005* (2013.01); *A61K 39/3955* (2013.01); *A61K 39/39541* (2013.01); *C07K 16/286* (2013.01); *C07K 14/705* (2013.01); *C07K 16/28* (2013.01); *C07K 2317/33* (2013.01); *C07K 2317/75* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 5,814,478 | A | 9/1998 | Valenzuela et al. |
| 6,342,220 | B1 | 1/2002 | Adams et al. |
| 6,413,740 | B1 | 7/2002 | Valenzuela et al. |
| 6,737,249 | B1 | 5/2004 | Carter et al. |
| 6,852,838 | B2 | 2/2005 | Valenzuela et al. |
| 7,816,322 | B2 | 10/2010 | Fallon et al. |
| 8,138,154 | B2 * | 3/2012 | Fallon ................. A61K 38/1709 424/184.1 |
| 2010/0130405 | A1 * | 5/2010 | Fallon ................. A61K 38/1709 514/20.9 |

OTHER PUBLICATIONS

Hegedus et al (2008. J Physiol. 586(14): 3337-3351).*
Phillips, 2001. J Pharm Pharmacology 53: 1169-1174.*
Scarrott et al, 2015. Expert Opin Biol Therapy, on-line version, pp. 1-13.*
DeChiara et al., "The receptor tyrosine kinase MuSK is required for neuromuscular junction formation in vivo", Cell, 1996, 85, 501-512.
Gomez et al., "The extracellular region of Lrp4 is sufficient to mediate neuromuscular synapse formation", Developmental Dynamics, 2011, 240, 2626-2633.
Narai et al., "Early detachment of neuromuscular junction proteins in ALS mice with SODG93A mutation", Neurology International, 2009, 1, e16.
Gautam et al., "Defective neuromuscular synaptogenesis in agrin-deficient mutant mice", Cell, 1996, 85, 525-535.
Herbst et al. "The juxtamembrane region of MuSK has a critical role in agrin-mediated signaling", The EMBO Journal 19, 2000, 67-77.
Hesser et al., "Synapse disassembly and formation of new synapses in postnatal muscle upon conditional inactivation of MuSK", Molecular and Cellular Neurosciences 31, 2006, 470-480.
Kim et al., "MuSK controls where motor axons grow and form synapses", Nature Neuroscience 11, 2008, 19-27.
Kim et al., "Lrp4 is a receptor for Agrin and forms a complex with MuSK", Cell 135, 2008, 334-342.
Kong et al., "Inhibition of synapse assembly in mammalian muscle in vivo by RNA interference", EMBO reports 5, 2004, 183-188.
Lin et al., "Distinct roles of nerve and muscle in postsynaptic differentiation of the neuromuscular synapse", 2001, Nature 410, 1057-1064.
Lin et al., "Neurotransmitter acetylcholine negatively regulates neuromuscular synapse formation by a Cdk5-dependent mechanism", Neuron 46, 2005, 46:569-579.
Stiegler et al., "Crystal structure of the frizzled-like cysteine-rich domain of the receptor tyrosine kinase MuSK", Journal of Molecular Biology, 2009, 393, 1-9.
Watty et al., "The in vitro and in vivo phosphotyrosine map of activated MuSK", Proceedings of the National Academy of Sciences of the United States of America, 2000, 97, 4585-4590.
Weatherbee et al., "LDL-receptor-related protein 4 is crucial for formation of the neuromuscular junction", Development , 2006,133, 4993-5000.
Xie et al., "Direct demonstration of MuSK involvement in acetylcholine receptor clustering through identification of agonist ScFv", Nature Biotechnology, 1997,15, 768-771.
Zhang et al., "LRP4 serves as a coreceptor of agrin", Neuron, 2008, 60, 285-297.

(Continued)

*Primary Examiner* — Zachary Howard
(74) *Attorney, Agent, or Firm* — Klauber & Jackson LLC

(57) ABSTRACT

Agents, compositions, and medicaments that pertain to modulating the activity of muscle specific kinase receptor (MuSK) and methods and uses thereof to modulate MuSK activity are encompassed herein. Also encompassed are screening assays to identify modulators of MuSK activity. Agents identified using the screening assays described herein are envisioned for use as therapeutics, alone or in compositions or in medicaments, to alleviate or delay motor dysfunction in subjects afflicted with a disorder associated with nerve terminal loss or fragmentation, such as amyotrophic lateral sclerosis, sarcopenia, or anti-MuSK myasthenia gravis.

8 Claims, 8 Drawing Sheets

(56) References Cited

OTHER PUBLICATIONS

Zhang et al., "Agrin binds to the N-terminal region of Lrp4 protein and stimulates association between Lrp4 and the first immunoglobulin-like domain in muscle-specific kinase (MuSK)", The Journal of Biological Chemistry, 2011, 286, 40624-40630.

Cornish et al., "Globular domains of agrin are functional units that collaborate to induce acetylcholine receptor clustering", J Cell Sci, 1999, 112:1213-1223.

Patel et al., "T-shaped arrangement of the recombinant agrin G3-IgG Fc protein", Protein Sci, 2011, 20:931-940.

Yumoto et al., "Lrp4 is a retrograde signal for presynaptic differentiation at neuromuscular synapses", Nature, 2012, 489:438-442.

Zhou et al., "Distinct domains of MuSK mediate its abilities to induce and to associate with postsynaptic specializations", The Journal of Cell Biology, 1999, 146:1133-1146.

Miller TM et al (2006) Gene transfer demonstrates that muscle is not a primary target for non-cell-autonomous toxicity in familial amyotrophic lateral sclerosis Proc Natl Acad Sci 103(51):19546-19551.

Pasinelli P et al (2006) Molecular biology of amyotrophic lateral sclerosis: insights from genetics Nature Rev Neurosci 7:710-723.

Valenzuela DM et al (1995) Receptor tyrosine kinase specific for the skeletal muscle lineage: expression in embryonic muscle, at the neuromuscular junction, and after injury Neuron 15:573-584.

\* cited by examiner

A

B

The copy number of the *SOD1G93A* transgene was measured by real time PCR, which showed the the copy number did not change over multiple generations and the course of the experiments.

Figure 8

```
                     VH
                        F1                                  CDR1    F2
SEQ ID NO: 5    1  MAQVQLQESGGEMKKPGESLKISCKGYGYSFATSWIGWVRQMPGRGLEWM
SEQ ID NO: 6    1  MAEVQLVQSGGGLVKPGGSLRLSCAASGFTFSDYYMSWIRQAPGKGLEWV
SEQ ID NO: 7    1  MAEVQLVQSGGGVVQPGGSLSLSCAVSGITLRTYGMHWVRQAPGKGLEWV
SEQ ID NO: 8    1  MAQVQLVQSGGGLVRPGGSLSLSCAVSGITLRTYGMHWVRQAPGKGLEWV
SEQ ID NO: 9    1  MAQVQLVESGGGLVKPGGSLRLSCAASGFTFSSHNMNWVRQAPGKGLEWV
SEQ ID NO: 10   1  MAQVQLQQSGPGLVKPSETLSLTCTVSGDSISSYYWSWIRQPPGKGLEWI

CDR2                       F3
SEQ ID NO: 5   51  AIMYPGNSDTRHNPSFEDQVTMSADTSINTAYLQWSSLKASDTAMYYCAR
SEQ ID NO: 6   51  SYISSSGSTIYYADSVKGRFTISRDNSKNTLYLQMNSLRAEDTAVYYCAR
SEQ ID NO: 7   51  AGISFDGRSEYYADSVKGRFTISRDNSKNTLYLQMNSLRAEDTAVYYCAR
SEQ ID NO: 8   51  AGISFDGRSEYYADSVQGRFTISRDSSKNTLYLQMNSLRAEDTAVYYCAR
SEQ ID NO: 9   51  SSISSSSSYIYYADSVKGRFTISRDNAKNSLYLQMNSLRAEDTAVYYCAR
SEQ ID NO: 10  51  GYIYYSGS-TNYNPSLKSRVTISVDTSKSQFSLKLSSVTAADTAVYYCAR

CDR3       F4                    VL    F1
SEQ ID NO: 5  101  AGVAGGAFDLWGKGTMVTVSSGGGGSGGGGSGGGGSQSVLTQ-PASVSGS
SEQ ID NO: 6  101  -WSGEDAFDIWGQGTMVTVSSGGGGSGGGGSGGGGSDIVMTQSPSTLSAS
SEQ ID NO: 7  101  -DRGSYGMDVWGRGTMVTVSSGGGGSGGGGSGGGGSDIQMTQSPSTLSAS
SEQ ID NO: 8  101  -G-AHYGFDIWGQGTMVTVSSGGGGTGGGGSGGGGSDIQMTQSPSTLSAS
SEQ ID NO: 9  101  -DRGSTGMDVWGRGTLVTVSSGGGGSGGGGSGGGGSDIQMTQSPSTLSAS
SEQ ID NO: 10 100  ----GRYFDVWGRGTMVTVSSGGGGSGGGGSGGGGSSYVLTQ-PPSVSGS

CDR1          F2                 CDR2
SEQ ID NO: 5  150  PGQSITISCTGTSSGVGGYNYVSWYQQHPGKAPKLLIYGNSNRPSGVPDR
SEQ ID NO: 6  150  VGDRVAITCRASE---GIYHWLAWYQQKPGKAPKLLIYKASSLASGAPSR
SEQ ID NO: 7  150  IGDRVTITCRASE---GIYHWLAWYQQKPGKAPKLLIYKASSLASGAPSR
SEQ ID NO: 8  149  IGDRVTITCRASE---GIYHWLAWYQQKPGKAPKLLIYKASSLASGAPSR
SEQ ID NO: 9  150  IGDRVTITCRASE---GIYHWLAWYQQKPGKAPKLLIYKASSLASGAPSR
SEQ ID NO: 10 145  PGQSITISCTGTSSDVGGYNYVSWYQQHPGKAPKLMIYEGSKRPSGVSNR

F3                         CDR3       F4
SEQ ID NO: 5  200  FSASKSGNTASLTISGLQAEDEADYFCSTYAPPGIIMFGGGTKLTVLGAA
SEQ ID NO: 6  197  FSGSGSGADFTLTISSLQPDDFATYYCQQYSNYPL-TFGGGTKLEVKRAA
SEQ ID NO: 7  197  FSGSGSGTDFTLTISSLQPDDFATYYCQQYSNYPL-TFGGGTKLEILRAA
SEQ ID NO: 8  196  FSGSGSGTDFTLTISSLQPDDFATYYCQQYSNYPL-TFGGGTELEIKRAA
SEQ ID NO: 9  197  FSGSGSGTDFTXTISSLQPDDFATYYCQQYSNYPL-TFGGGTKLEIKRAA
SEQ ID NO: 10 195  FSGSKSGNTASLTISGLQAEDEADYYCSSYTTRSTRVFGGGTKLTVLGAA
```

METHOD OF TREATING MOTOR NEURON DISEASE WITH AN ANTIBODY THAT AGONIZES MUSK

CROSS REFERENCE TO RELATED APPLICATIONS

The present application is a National Stage Application which claims priority under 35 U.S.C. §120 from co-pending PCT Application No. PCT/US2012/065023 filed Nov. 14, 2012, which in turn claims priority under from 35 U.S.C. §119(e) from U.S. Provisional Application Ser. No. 61/693,857, filed Aug. 28, 2012 and U.S. Provisional Application Ser. No. 61/559,309, filed Nov. 14, 2011, each of which applications are herein specifically incorporated by reference in their entireties.

FIELD OF INVENTION

The compositions and methods described herein relate to muscle specific kinase receptor (MuSK) and modulation thereof, as well as to screening assays to identify modulators of MuSK activity. Agents identified using the screening assays described herein are envisioned for use as therapeutics to alleviate or delay motor dysfunction in subjects afflicted with a disorder associated with nerve terminal loss or fragmentation, including sarcopenia, amyotrophic lateral sclerosis and anti-MuSK myasthenia gravis.

BACKGROUND OF INVENTION

Our ability to move and breathe depends upon the neuromuscular synapse. As such, the neuromuscular synapse is the single synapse essential for survival. Neuromuscular synapse formation is a multi-step process requiring coordinated interactions between motor neurons and muscle fibers, which eventually lead to the formation of a highly specialized postsynaptic membrane and a highly differentiated nerve terminal. As a consequence, acetylcholine receptors (AChRs) become highly concentrated in the postsynaptic membrane and arranged in perfect register with active zones in the presynaptic nerve terminal, and thus ensure fast, robust and reliable synaptic transmission. The signals and mechanisms responsible for this process are poorly understood but require MuSK, a receptor tyrosine kinase that is expressed in skeletal muscle, Agrin, a motor neuron-derived ligand that stimulates MuSK phosphorylation, and Lrp4, the receptor for Agrin. These genes play critical roles in synaptic differentiation, as synapses do not form in their absence, and mutations in MuSK or downstream effectors lead to a reduced number of AChRs at synapses and are a major cause of a group of neuromuscular disorders, termed congenital myasthenia. Moreover, auto-antibodies to AChRs, MuSK or Lrp4, which cause accelerated degradation of AChRs and structural disorganization of the synapse, are responsible for myasthenia gravis.

The mechanisms that control and stabilize connections between motor axon terminals and muscle fibers are poorly understood, but the maintenance of neuromuscular synapses is essential to sustain synaptic transmission and prevent muscle atrophy. In amyotrophic lateral sclerosis (ALS), a loss of motor axon terminals, which causes muscle denervation, is the earliest known sign of disease. ALS is a devastating, neurodegenerative disorder, with a midlife onset, characterized by the progressive loss of upper and lower motor neurons and leading to relentless, lethal paralysis. Following diagnosis of ALS, either sporadic or familial, the time course of disease progression varies in an unpredictable manner. Dominant mutations in superoxide dismutase (SOD1) are responsible for 2% of the cases of ALS. Transgenic mice expressing mutant forms of SOD1 develop a paralytic motor neuron disease, which exhibits all of the hallmark features of ALS.

A progressive and gradual withdrawal of motor axon terminals accompanies aging, compromising synaptic function and causing muscle atrophy, or sarcopenia. Once this cycle is initiated, muscle atrophy and deterioration are further exacerbated, as muscle atrophy and a loss of muscle strength reduce physical activity and exercise, which decreases synaptic activity still further. Sarcopenia is a major and debilitating consequence of aging. Moreover, because sarcopenia reduces physical activity, sarcopenia compromises health by contributing to a wide range of complications in multiple organ systems.

The citation of references herein shall not be construed as an admission that such is prior art to the present invention.

SUMMARY OF THE INVENTION

The present inventor sought to determine whether increasing MuSK activity might be sufficient to stabilize synapses that are weakened, irrespective of the mechanism underlying the instability. To this end, the present inventor investigated whether MuSK over-expression might stabilize synapses in mice carrying dominant mutations in SOD1. Mice carrying transgenes with a mutation in SOD1, namely SOD1G93A, serve as a model for ALS, as the pathological and clinical signs of disease in this mouse model replicate those in ALS. In particular, a loss of neuromuscular synapses and the withdrawal of motor axons is the earliest sign of disease in the mouse model and in familial and sporadic forms of ALS. Such muscle denervation leads to paralysis, respiratory failure and ultimately premature death.

The present inventor crossed MuSK-L mice with SOD1G93A mice, which generated four types of progeny: (1) wild-type mice; (2) MuSK-L; (3) SOD1G93A; and (4) MuSK-L; SOD1G93A mice. Although MuSK over-expression did not significantly prolong the longevity of SOD1G93A mice, MuSK over-expression substantially delayed denervation of skeletal muscle in MuSK-L; SOD1G93A mice relative to SOD1G93A mice. Indeed, the loss of neuromuscular synapses was far less in MuSK-L; SOD1G93A mice than SOD1G93A mice during a forty day period (P120-P160) when synapses disassemble in SOD1G93A mice. MuSK over-expression also substantially and similarly improved motor function of SOD1G93A mice, as assessed by an improvement in their ambulatory behavior and an increase in muscle strength during this forty day period when SOD1G93A mice showed severe signs of motor dysfunction and muscle weakness.

The present findings, therefore, demonstrate that increasing MuSK activity in muscle is sufficient to delay synaptic loss and motor dysfunction in a mouse model of ALS. Accordingly, increasing MuSK activity in humans with ALS has the potential to alleviate and delay motor dysfunction, allowing ALS patients to function without assistance for extended periods of time.

Moreover, these findings raise the possibility that increasing MuSK activity may alleviate motor dysfunction in other disorders associated with nerve terminal loss or fragmentation, including sarcopenia. Further, as disease-causing auto-antibodies to MuSK interfere with MuSK function, increasing MuSK activity in patients with anti-MuSK auto-immune myasthenia gravis may likewise alleviate the weakness and fatigue that are hallmark features of this disease.

Accordingly, in an aspect of the invention, a method for delaying motor dysfunction in a subject is presented, the method comprising: administering an agent that increases muscle specific receptor kinase (MuSK) activity to the subject in a therapeutically effective amount sufficient to increase MuSK activity in the subject and thereby improve motor function in the subject. Also encompassed herein is a method for treating a disease or condition associated with synaptic loss and/or motor dysfunction in a subject, the method comprising administering a therapeutically effective amount of an agent that increases MuSK activity to the subject. In another aspect, a method for preserving neuromuscular synapses in a subject is presented, the method comprising: administering an agent that increases muscle specific receptor kinase (MuSK) activity to the subject in a therapeutically effective amount sufficient to increase MuSK activity in the subject and thereby preserve neuromuscular synapses in the subject.

Use of an agent that increases MuSK activity for the treatment of a disease or condition associated with synaptic loss and/or motor dysfunction in a subject comprising administering a therapeutically effective amount of the agent to the subject is also encompassed. An agent that increases MuSK activity for use in treating a disease or condition associated with synaptic loss and/or motor dysfunction in a subject is also encompassed, wherein the agent is administered to the subject in a therapeutically effective amount so as to treat the disease or condition associated with synaptic loss and/or motor dysfunction in the subject. Use of an agent that increases MuSK activity to delay motor dysfunction in a subject comprising administering a therapeutically effective amount of the agent to the subject is also envisioned. An agent that increases MuSK activity for use in delaying motor dysfunction in a subject is further envisioned, wherein the agent is administered to the subject in a therapeutically effective amount to delay motor dysfunction in the subject.

Also encompassed herein is use of an agent that increases MuSK activity for the preparation of a medicament for treating a disease or condition associated with synaptic loss and/or motor dysfunction in a subject or for delaying motor dysfunction in a subject.

In an embodiment of the methods and uses described herein, the agent is a polypeptide, an antibody or antibody fragment, a polynucleotide, a chemical compound, or a small molecule. In a more particular embodiment, the antibody or antibody fragment increases MuSK activity upon binding to MuSK.

In another embodiment of the methods and uses described herein, the agent is a polypeptide comprising or consisting of the amino acid sequence of agrin or Lrp4 or functional fragments thereof. Exemplary amino acid sequences of human agrin are designated herein as SEQ ID NO: 2. Exemplary amino acid sequences of human Lrp4 are designated herein as SEQ ID NO: 4.

In a particular embodiment, the delay in motor dysfunction is measurable by determining innervation levels. In another embodiment, administering the agent maintains innervation levels in the subject.

In yet another embodiment, administering the agent stabilizes motor axon synapses or increases the number of motor axon synapses in the subject.

In a particular embodiment, the subject is suffering from amyotrophic lateral sclerosis, sarcopenia, or myasthenia gravis. In a more particular embodiment, the subject is suffering from amyotrophic lateral sclerosis. More particularly still, the subject may be a mammal (for example, a mouse, rat, or primate). In a more particular example, the mammal is a mouse comprising a transgene with a mutation in SOD1. In an even more particular embodiment, the mouse comprises a transgene with a mutation in SOD1, wherein the transgene is SOD1G93A. In another particular embodiment, the mammal is a human.

Also encompassed herein is a method for screening to identify an agent that increases MuSK activity, the method comprising: contacting populations of myotubes with at least one agent in vitro and assaying the MuSK activity in the populations after the contacting, wherein an increase in MuSK activity in a population of myotubes following contact with the at least one agent relative to that following contact with a control agent identifies the at least one agent as an agent that increases MuSK activity.

In a particular embodiment of the screening method, the myotubes are differentiated from muscle cells grown in vitro. In a more particular embodiment, the myotubes or muscle cells are isolated from a mouse comprising a transgene with a mutation in SOD1. In an even more particular embodiment, the mouse comprises a transgene with a mutation in SOD1, wherein the transgene is SOD1G93A.

In an embodiment of the screening method, the MuSK activity is measured by detecting MuSK phosphorylation levels and/or clustering of acetylcholine receptors (AChR). More particularly, an increase in MuSK activity may be measured by detecting increased levels of MuSK phosphorylation and/or clustering of acetylcholine receptors (AChR) following contacting with the at least one agent.

In another particular embodiment of the screening method, the at least one agent is a polypeptide, an antibody or antibody fragment, a polynucleotide, a chemical compound, or a small molecule.

In another embodiment of the screening methods described herein, the agent is a polypeptide comprising or consisting of the amino acid sequence of agrin or Lrp4 or functional fragments thereof. Exemplary amino acid sequences of human agrin are designated herein as SEQ ID NO: 2. Exemplary amino acid sequences of human Lrp4 are designated herein as SEQ ID NO: 4.

The screening method may further comprise a secondary assay, wherein the at least one agent identified as an agent that increases MuSK activity in the primary screen is evaluated in a secondary assay wherein MuSK is immunoprecipitated from cell lysates and analyzed by probing Western blots with antibodies to phosphotyrosine.

Also encompassed herein is a method for delaying motor dysfunction in a subject, the method comprising: administering an agent that increases muscle specific receptor kinase (MuSK) activity as identified by a screening method described herein to the subject in a therapeutically effective amount sufficient to increase MuSK activity in the subject and thereby improve motor function in the subject.

In a further embodiment, a method for preserving neuromuscular synapses in a subject is envisioned, the method comprising: administering an agent that increases muscle specific receptor kinase (MuSK) activity as identified by a screening method described herein to the subject in a therapeutically effective amount sufficient to increase MuSK activity in the subject and thereby preserve neuromuscular synapses in the subject.

In a still further embodiment, use of an agent that increases muscle specific receptor kinase (MuSK) activity as identified by a screening method described herein in the preparation of a medicament for delaying motor dysfunction in a subject is envisioned, wherein the medicament is administered in a therapeutically effective amount that increases MuSK activity in the subject and thereby improves motor function in the subject.

In yet another embodiment, use of an agent that increases muscle specific receptor kinase (MuSK) activity as identified by a screening method described herein in the preparation of a medicament for preserving neuromuscular synapses in a subject is envisioned, wherein the medicament is administered in a therapeutically effective amount that increases MuSK activity in the subject and thereby preserves neuromuscular synapses in the subject.

Yet another embodiment encompasses an agent that increases muscle specific receptor kinase (MuSK) activity as identified by a screening method described herein for use in delaying motor dysfunction in a subject, wherein the agent is administered to the subject in a therapeutically effective amount sufficient to increase MuSK activity in the subject and thereby improve motor function in the subject.

A further embodiment encompasses an agent that increases muscle specific receptor kinase (MuSK) activity as identified by a screening method described herein for use in preserving neuromuscular synapses in a subject, wherein the agent is administered to the subject in a therapeutically effective amount sufficient to increase MuSK activity in the subject and thereby preserve neuromuscular synapses in the subject.

Other objects and advantages will become apparent to those skilled in the art from a review of the following description which proceeds with reference to the following illustrative drawings.

DETAILED DESCRIPTION OF THE INVENTION

Figure 1:
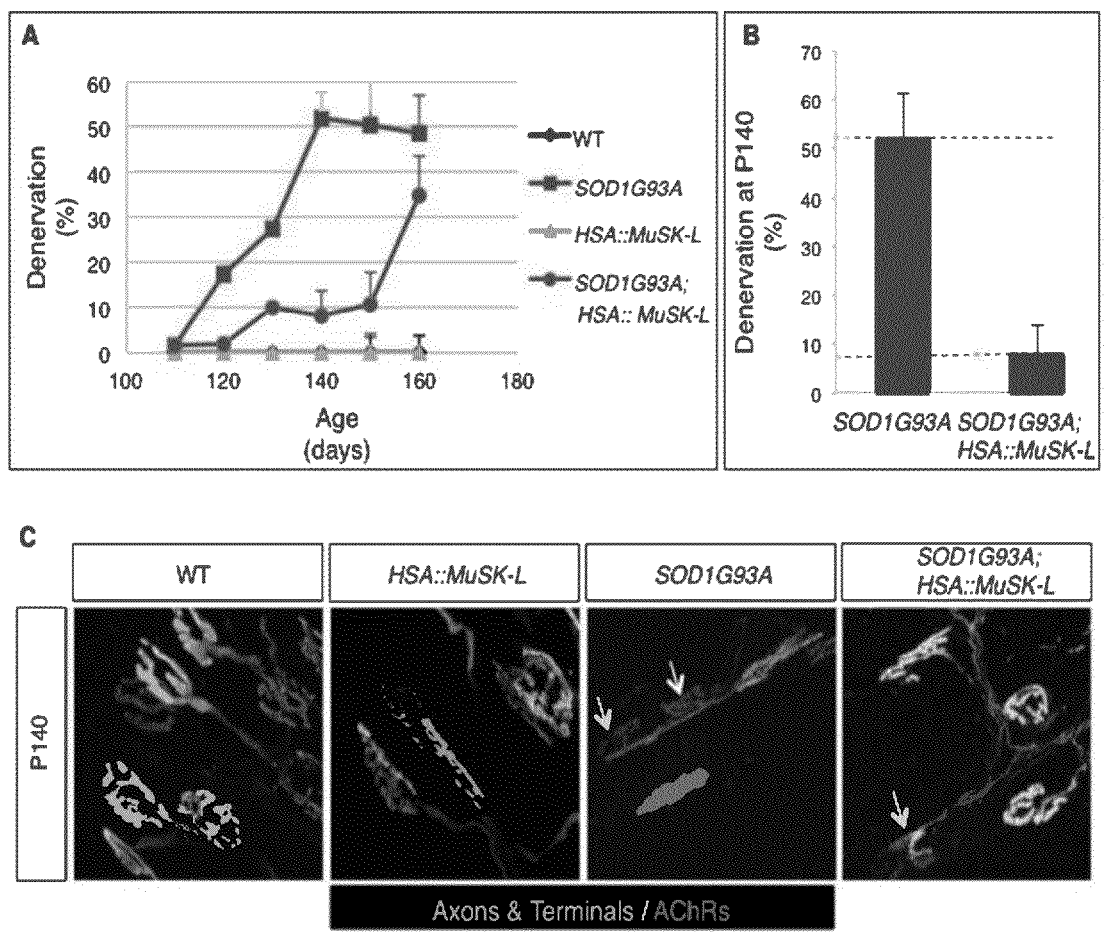
FIG. 1 shows that MuSK over-expression delays the onset and reduces the extent of denervation in SOD1G93A mice. A) Denervation becomes evident at P120 in SOD1G93A mice and at P130 in SOD1G93A mice over-expressing MuSK. The extent of denervation remains lower in mice over-expressing MuSK through P150. B) At P140, only 8% of synapses are denervated in SOD1G93A mice over-expressing MuSK, whereas 52% of synapses are denervated in SOD1G93A mice. C) Images of synapses from P140 mice stained with α-BGT to label AChRs and antibodies to Neurofilament and Synapsin to label motor axons and nerve terminals. Staining for Synapsin and AChRs overlap at innervated synapses, whereas Synapsin staining is absent from denervated synapses, which retain a high density of AChRs.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [RI. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific binding member" describes a member of a pair of molecules, which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain, which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv (ScFv) Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J. Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The term "variable" refers to the fact that certain portions of the variable domains differ extensively in sequence among antibodies and are used in the binding and specificity of each particular antibody for its particular antigen. Variability is not, however, evenly distributed throughout antibody variable domains and is concentrated in three segments called complementarity determining regions (CDRs) or hypervariable regions which are found in both the light chain and heavy chain variable domains. The more highly conserved portions of variable domains are referred to as the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of an antibody. The constant domains are not involved directly in antigen binding, but exhibit various effector functions, such as participation of the antibody in antibody-dependent cellular toxicity.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-growth hormone receptor specific antibody. The other binding domain may be an antibody that recognizes or targets a particular cell type, as in a muscle, neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine, or mitotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "activating antibody" refers an antibody that upon binding specifically to an antigen for which it has specificity activates the antigen. With respect to an activating antibody specific for MuSK, upon binding MuSK, the activating antibody would activate MuSK, thus leading to MuSK phosphorylation and subsequent clustering of AChR. Exemplary such antibodies include
agonist antibodies #13 and #22 described herein. See also Xie et al. (1997), the entire content of which is incorporated herein in its entirety.

The term "adjuvant" refers to a compound or mixture that enhances the immune response, particularly to an antigen. An adjuvant can serve as a tissue depot that slowly releases the antigen and also as a lymphoid system activator that nonspecifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum.* Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance an immune response (e.g., a vaccine-induced immune response), be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 µg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease Si), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding protein or peptide sequences as provided herein, or comprising sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the sequences encoding the protein or peptide sequences of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups

Alanine, Valine, Leucine, Isoleucine, Proline, Phenylalanine, Tryptophan, Methionine Amino Acids with Uncharged Polar R Groups Glycine, Serine, Threonine, Cysteine, Tyrosine, Asparagine, Glutamine Amino Acids with Charged Polar R Groups (Negatively Charged at pH 6.0)

Aspartic acid, Glutamic acid

Basic Amino Acids (Positively Charged at pH 6.0)

Lysine, Arginine, Histidine (at pH 6.0)

Another grouping may be those amino acids with phenyl groups:

Phenylalanine, Tryptophan, Tyrosine

Another grouping may be according to molecular weight (i.e., size of R groups):

| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces beta-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural binder to a binding site.

The term 'assay' means any process used to measure a specific property of a compound or agent. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Subject' includes humans. The terms "human," "patient" and "subject" may be used interchangeably herein.

'Therapeutically effective amount' means that amount of a drug, compound, antimicrobial, antibody, or pharmaceutical agent that will elicit the biological or medical response of a subject that is being sought by a medical doctor or other clinician. As an example, with regard to immune response, the term "effective amount" is intended to include an effective amount of a compound or agent that will bring about a biologically meaningful decrease in the amount of or extent of immune response, activation indicator and/or a biologically meaningful increase in the amount or extent of dendritic cell, T cell and/or B cell effects. The phrase "therapeutically effective amount" is used herein to mean an amount sufficient to prevent, and preferably reduce by at least about 30 percent, more preferably by at least 50 percent, most preferably by at least 90 percent, a clinically significant change in the immune response or immune cell indicator or response, or in a patient's response to an antigen, vaccine, or other immune agent, or in a patient's clearance of an infectious agent, or other feature of pathology such as for example, elevated activated T or B cells, activated DC cell count, fever or white cell count.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

B. DETAILED DISCLOSURE

Previous investigations have shown that neuromuscular synapses form in mice lacking Agrin, but these synapses are unstable, leading to axon withdrawal and neonatal lethality. The present inventor and his colleagues found that a threefold increase in MuSK expression, conferred by a MuSK-L transgene, rescued these neuromuscular synapses and prevented the neonatal lethality of agrin mutant mice (Kim and Burden, 2008). These studies demonstrated that a modest increase in MuSK activity is sufficient to prevent the disassembly of neuromuscular synapses that occurs in the absence of Agrin.

The experiments described herein were performed to determine whether MuSK over-expression might prevent motor axon withdrawal in other mechanistically distinct instances of synaptic dysfunction. To address this issue, the present inventor crossed the MuSK transgene into a mouse model of ALS (SOD1G93A mice), wherein mice die prematurely due to motor axon withdrawal from muscle and ultimately motor neuron death. In experiments described herein, the present inventor surprisingly found that MuSK over-expression delays muscle denervation by forty days, preserving motor behavior that would otherwise be severely compromised in SOD1G93A mice. These results suggest that increasing MuSK activity might delay symptoms and therefore be beneficial for patients with ALS.

The finding that MuSk over-expression could partially rescue SOD1G93A mice was surprising for a variety of reasons. To begin, ALS is a motor neuron disease, whereas MuSK is expressed in muscle, not motor neurons. Thus, it is surprising that over-expression of any protein in a cell type (i.e., muscle cell) other than the primarily impaired cell type could compensate, even partially, for the genetic defects of the primary cell type involved in ALS. Moreover, motor neurons in ALS are compromised in numerous ways. The deficiencies in, for example, mitochondrial function and axonal transport in ALS motor neurons compromise motor neuron function and activity so severely that it could not be envisioned with any degree of likelihood that synapse preservation could be preserved by increased expression of any single protein. This is especially apparent with respect to increasing expression of a protein in cells other than motor neurons wherein the activity of the protein can have no direct effect on motor neuron activity/function. Given the above, it is surprising that over-expression of MuSK in muscle cells can preserve neuromuscular synapses in the context of a genetic background characterized by motor neurons having severely impaired activity/function.

As described herein, the present inventor crossed MuSK-L mice with SOD1G93A mice, which generated four types of progeny: (1) wild-type mice; (2) MuSK-L; (3) SOD1G93A; (4) MuSK-L; SOD1G93A mice. The longevity of these mice was assessed and MuSK over-expression, such as that observed in MuSK-L mice, did not significantly prolong the longevity of SOD1G93A mice. However, MuSK over-expression substantially delayed the onset and decreased the extent of muscle denervation in MuSK-L; SOD1G93A mice relative to SOD1G93A mice, as reflected by the observation that substantially more neuromuscular synapses appeared intact over a forty day period (P120-P160) when synapses disassemble in SOD1G93A mice. Consistent with these histological findings, MuSK over-expression substantially improved motor function of SOD1G93A mice in that MuSK-L; SOD1G93A mice exhibited greater ambulatory behavior and muscle strength, as assessed on a rotarod and by grip strength, over the same 40 day period, when SOD1G93A mice showed severe signs of motor dysfunction and muscle weakness.

The present findings indicate that increasing MuSK activity in muscle is sufficient to delay the onset and decrease the extent of synaptic loss and improve motor dysfunction in a mouse model of ALS. As such, increasing MuSK activity in humans with ALS has the potential to alleviate and delay motor dysfunction, allowing ALS patients to function without assistance for a more prolonged period of time.

To pursue these findings further, studies are ongoing to evaluate the ability of other means to activate MuSK in vivo to alleviate motor dysfunction in ALS patients. Several possibilities for MuSK activators having potential utility in in vivo applications include, without limitation: (1) Agrin and Lrp4, which are known MuSK activators and can be tested in the mouse model described herein; (2) Antibodies that activate MuSK in cultured muscle [see Xie et al. Nat. Biotech. 1997 15:768) and can be tested in vivo in, for example, the mouse model described herein; and (3) using small molecule activators of MuSK identified in the screening assays described herein. Fragments thereof, such as ScFv can also be tested using similar and/or identical assays.

Moreover, these findings raise the possibility that increasing MuSK activity may alleviate motor dysfunction in other disorders associated with nerve terminal loss or fragmentation, irrespective of the underpinning mechanistic causes that led to the nerve terminal loss or fragmentation. Such disorders include, for example, sarcopenia. Increasing MuSK activity may also improve motor function in auto-immune, anti-MuSK myasthenia gravis.

Amyotrophic Lateral Sclerosis

ALS is a devastating neurodegenerative disease, culminating in the death of motor neurons, complete muscle paralysis and lethal respiratory failure, without cognitive impairment, within five years of diagnosis (Fischer et al., 2004; Pasinelli and Brown, 2006; Schaefer et al., 2005). The incidence of disease is ~1/7,500, similar to muscular dystrophy or myasthenia gravis. The mechanisms responsible for neuronal cell death are poorly understood, and studies designed to inhibit motor neuron cell death, either by blocking cell death pathways or providing broadly acting growth factors, have had little impact on disease progression (Kostic et al., 1997; Pun et al., 2006; Sagot et al., 1995). As such, there are no therapies to cure let alone slow disease progression.

Dominant mutations in SOD1, TDP-43, FUS, and the recently discovered C9orf72 gene are responsible for familial forms of ALS and together represent ~17% of all cases of ALS (Chen-Plotkin et al., 2010; Kwiatkowski et al., 2009; Majounie et al., 2012; Pasinelli and Brown, 2006; Renton et al., 2011; Vance et al., 2009). The pathological hallmarks of the disease are well replicated in mice that overexpress mutant forms of SOD1 in motor neurons, providing an excellent model system for studying the pathology of ALS and identifying approaches to treat this devastating disease (Pasinelli and Brown, 2006). Although cell types other than motor neurons, including grey matter oligodendrocytes and microglia contribute to disease onset and progression (Ilieva et al., 2009; Kang et al., 2010), expression of mutant forms of SOD1 in skeletal muscle does not cause disease (Miller et al., 2006). As such, dominant mutations in SOD1 act largely in an autonomous manner within motor neurons, consistent with the idea that ALS is primarily a disease of upper and lower motor neurons.

Sarcopenia

Sarcopenia, the atrophy and deterioration of skeletal muscle that leads to weakness and fatigue, is a major and debilitating consequence of aging. Moreover, sarcopenia is a major driving force of aging, as sarcopenia reduces physical activity and thereby compromises health by contributing to a wide range of complications in multiple organ systems, including vascular, cardiac, pulmonary and skeletal systems. The factors that trigger sarcopenia are poorly understood, but most attention has been focused on the idea that an increase in proteasome activity in muscle causes an increase in protein breakdown and causes muscle atrophy. As such, sarcopenia is largely considered a muscle disease, not a synaptic disease.

Myasthenia Gravis

Myasthenia gravis is an auto-immune disease caused by auto-antibodies to synaptic proteins, including acetylcholine receptors (AChRs), MuSK & Lrp4, leading to muscle weakness. The prevalence in the US is 1/~7,500. Auto-antibodies to AChRs stimulate accelerated degradation of AChRs and cause complement-mediated structural disorganization of the synapse. In contrast, auto-antibodies to MuSK are IgG4, which are functionally monovalent and fail to engage complement, suggesting that they interfere with MuSK function, rather than recruiting complement. Our recent, unpublished studies, in collaboration with the Verschuuren lab in Leiden, Netherlands, show that disease-causing auto-antibodies to MuSK interfere with the ability of MuSK to bind Lrp4, and therefore provide a ready explanation for the inhibitory effects of these antibodies.

Therapeutic Strategies

Several types of therapeutic strategies are envisioned: (1) Since Agrin is an activator of MuSK, supplying Agrin may prove therapeutic in patients with ALS. As indicated above, the SOD1G93A mouse model described herein is a suitable screening system in which to investigate therapeutic efficacy of agrin and agrin biological mimetics. (2) Since Lrp4 binds and activates MuSK, fragments of Lrp4 that bind MuSK or mimics of Lrp4 may prove therapeutic in patients with ALS. As indicated above, the SOD1G93A mouse model described herein can be used as an initial screening system to test efficacy. (3) Antibodies to Lrp4 or MuSK that stimulate MuSK may prove therapeutic in patients with ALS. This idea could be first tested using the SOD1G93A mouse model described here. (4) Small molecules that activate MuSK may prove therapeutic in patients with ALS. Such activators might be identified by screening for small molecules that stimulate MuSK phosphorylation in cultured cells.

Agrin is a large heparin sulphate proteoglycan with multiple domains, which is located in the extracellular matrix. It is involved in neuromuscular junction formation, wherein it directs clustering of postsynaptic molecules, including acetylcholine receptors (AChRs). This activity is conferred by the C-terminal portion of the protein, which consists of three laminin-like globular domains (G-domains: G1, G2 and G3) and four EGF-like repeats. In a study to investigate the contributions of individual domains and alternate splicing to agrin activity, single G-domains and covalently linked pairs of G-domains were expressed as soluble proteins and their AChR clustering activity assessed using cultured C2 myotubes. See Cornish et al. (J Cell Sci 1999 112:1213-1223), the entire content of which is incorporated herein by reference in its entirety.

This study revealed that only G3(8) exhibits detectable activity by itself, but all G-domains studied (G1, G2(0), G2(4), G3(0) and G3(8)) enhance G3(8) activity when physically linked to G3(8). This effect is most pronounced when G2(4) is linked to G3(8) and is independent of the order of the G-domains. The study also revealed that deletion of EGF-like repeats enhances activity and increasing the physical separation between linked G1 and G3(8) domains produces a significant increase in activity, whereas similar alterations to linked G2 and G3(8) domains are without effect. Clusters induced by two concatenated G3(8) domains were also shown to be significantly smaller than all other agrin forms studied. The study concluded that agrin G-domains are the functional units involved in AchR clustering and interact independently of their specific organization in this activity. See Cornish et al. (J Cell Sci 1999 112:1213-1223).

As described in Patel et al. (Protein Sci 2011 20:931-9400, the entire content of which is incorporated herein by reference in its entirety), the C-terminal G3 domain of agrin is critical for agrin function since it harbors an α-dystroglycan binding site and carries out acetylcholine receptor clustering activities. To further investigate its functionality, Patel et al. fused the G3 domain of agrin to an IgG Fc domain to produce a G3-Fc fusion protein. As further described therein, the G3-Fc protein forms a T-shaped molecule with the G3 domains extruding perpendicularly from the Fc scaffold. In light of the functional significance of the G3 domain, the G3-Fc fusion protein of Patel et al. and structurally similar fusion protein are exemplary agents to be tested in the screening assays described herein.

Accordingly, human agrin and functional fragments thereof are exemplary agents to be tested in the screening assays described herein. Human agrin and functional fragments, such as, for example, G3(8) alone or linked to G1, G2(0), G2(4), G3(0) and/or G3(8), are also envisioned as exemplary agents for use as MuSK activators in applications pertaining to methods for treating subjects in need thereof and for use in delaying motor dysfunction in a subject in need thereof, or for use in preserving neuromuscular synapses in a subject in need thereof. Exemplary nucleic and amino acid sequences are known in the art (see, e.g., GenBank Accession Number NM_198576.3 for human agrin mRNA) and presented herein as SEQ ID NOs: 1 and 2, respectively.

Further to the above, human Lrp4 and functional fragments thereof are also exemplary agents to be tested in the screening assays described herein. Human Lrp4 and functional fragments are also envisioned as exemplary agents for use as MuSK activators in applications pertaining to methods for treating subjects in need thereof and for use in delaying motor dysfunction in a subject in need thereof, or for use in preserving neuromuscular synapses in a subject in need thereof.

Exemplary nucleic and amino acid sequences are known in the art (see, e.g., GenBank Accession Number NM_002334.33 for human Lrp4 mRNA) and presented herein as SEQ ID NOs: 3 and 4, respectively.

Additional exemplary agents envisioned for testing in the screening assays described herein include activating antibodies immunospecific for MuSK. Xie et al. (Nat. Biotech. 1997 15:768), for example, describe monovalent scFv activating antibodies, as well as IgG counterparts of these antibodies to MuSK. In light of the above, it is clearly possible to screen and identify antibodies that are capable of acting as MuSK agonists. The content of Xie et al. (Nat. Biotech. 1997 15:768) is incorporated herein by reference in its entirety.

In accordance with standard practice in antibody technology, it is understood that full length antibodies or antigen binding fragments or variants thereof can be envisioned that comprise variable heavy (VH) and variable light (VL) chains of exemplary scFv fragments. It is, moreover, understood that some variation in framework sequences is tolerated and does not necessarily alter the binding properties or functional activity of antibodies or functional fragments or variants thereof as long as the CDR sequences, which are critical for binding specificity, are preserved. Functional properties of different regions of antibodies and functional fragments and variants thereof are known to those skilled in the art and described in, for example, Kabat et al., *Sequences of Proteins of Immunological Interest*, National Institutes of Health, Bethesda, Md. (1987).

Additional information pertaining to the exemplary scFvs described, including nucleic acid sequences encoding same and methods of making same, can be found, for example, in the Sequence Listing and Examples of U.S. Pat. No. 6,737, 249 and United States Patent Application Publication No. 2006/0177441, the entire content of each of which is incorporated herein by reference.

In one embodiment, screening assays described herein would require growing mouse muscle cell lines, such as, for example, C2 cells, and allowing the cells to differentiate to form myotubes. This is very straightforward. Cells would be plated in 96 well plates and treated with small molecule libraries. Since MuSK phosphorylation leads to clustering of acetylcholine receptors (AChR), which can be readily visualized by fluorescent microscopy, measuring AChR clustering would be the simplest means to identify small molecules that activate MuSK. Moreover, because AChR clustering is exceedingly rare in the absence of MuSK activation, it should be quite simple to distinguish a bona fide signal from noise. This primary assay would be followed-up with a secondary assay in which MuSK phosphorylation is directly measured by immunoprecipitating MuSK from cell lysates and probing Western blots with antibodies to phosphotyrosine.

Nucleic and amino acid sequences corresponding to MuSK are presented in U.S. Pat. Nos. 5,814,478; 6,413,740; and 6,852,838, the entire contents of each of which is incorporated herein in its entirety.

In one particular embodiment, with respect to the compounds or agents described herein, the compound/agent is administered alone or in conjunction with other compounds/ agents described herein or known to be efficacious in the treatment of a disorder associated with synaptic loss and motor dysfunction such as those described herein. In another aspect, pharmaceutical compositions comprising a compound/agent or a plurality of the compounds/agents described herein are administered to a subject in need thereof. Compounds and agents described herein may also be used in the preparation of a medicament for treating a disorder associated with synaptic loss and motor dysfunction such as those described herein.

In one embodiment, with respect to the method of treatment, use of an agent of compound, or preparation of a medicament, the disease or condition is a disorder associated with synaptic loss and motor dysfunction. Such disorders include amyotrophic lateral sclerosis (ALS), sarcopenia, and anti-MuSK myasthenia gravis. In a particular embodiment, the disease or condition is associated with nerve terminal loss or fragmentation, wherein such condition is amyotrophic lateral sclerosis.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds/agents are used as therapeutic agents for the treatment of conditions in mammals that are associated with synaptic loss and motor dysfunction. Such disorders include ALS, sarcopenia, and myasthenia gravis. Accordingly, the compounds and pharmaceutical compositions of this invention find use as therapeutics for preventing and/or treating a variety of conditions and disorders in mammals, including humans.

In a method of treatment aspect, this invention provides a method of treating a mammal susceptible to or afflicted with a condition or disorder associated with synaptic loss and motor dysfunction, which method comprises administering an effective amount of one or more of the pharmaceutical compositions just described.

In additional method of treatment aspects, this invention provides methods of treating a mammal susceptible to or afflicted with a condition or disorder causally related or attributable to synaptic loss. Such conditions and disorders include, ALS, sarcopenia, and myasthenia gravis. Such methods comprise administering an effective condition-treating or condition-preventing amount of one or more of the pharmaceutical compositions just described. In a particular embodiment thereof, the condition or disorder is ALS, sarcopenia, or anti-MuSK myasthenia gravis. In a more particular embodiment, the condition or disorder is ALS. In an even more particular embodiment, the condition or disorder is sarcopenia.

As a further aspect of the invention, the present compounds are provided for use as pharmaceuticals, especially in the treatment or prevention of the aforementioned conditions and diseases. Also provided herein is the use of the present compounds in the manufacture of a medicament for the treatment or prevention of one of the aforementioned conditions and diseases. Also encompassed is at least one compound or agent described herein for use in treating or preventing one of the aforementioned conditions and diseases. Further to the above, a combination of one or more of the compounds/agents described herein for a method of treating a condition or disorder causally related or attributable to synaptic loss in a subject is also encompassed herein.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., ALS, sarcopenia, and anti-MuSK myasthenia gravis, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg. Long term treatment of the above-mentioned diseases is envisioned to span ~5 years with respect to ALS, ~20 years with respect to sarcopenia, and >30 years with respect to anti-MuSK myasthenia gravis.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition. A skilled practitioner could, for example, treat a patient afflicted with ALS, for example, with a therapeutic regimen that included delivery of the compounds or compositions of the invention using an intramuscular injection for direct delivery to an affected muscle. Intraperitoneal (ip) and intravenous (iv) injection delivery modes are also envisioned for the treatment of diseases and conditions described herein, including ALS.

When used to prevent the onset of a condition or disorder causally related or attributable to synaptic loss, the compounds of this invention will be administered to a patient at risk for developing the condition or disorder, typically on the advice and under the supervision of a physician, at the dosage levels described above. Patients at risk for developing a particular condition generally include those with a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example I

Experimental Procedures

Animals

Mice overexpressing human SOD1 (B6.Cg-Tg(SOD1-G93A)1Gur/J) were purchased from Jackson Laboratory (Bar Harbor, Me.) and crossed with HSA::MuSK-L transgenic mice, which were also maintained on a C57BL/6J background (24). SOD1G93A mice were genotyped by PCR (5'-CATCAGCCCTAATCCATCTGA-3' and 5'-CGCGACTAACAATCAAAGTGA-3'). Primers for IL-2 were used as an internal control (5'-CTAGGCCACAGAATTGAAAGATCT-3' and 5'-GTAGGTGGAAATTCTAGCATCATCC-3').

HSA::MuSK-L transgenic mice express 3-fold more MuSK than wild-type mice (Kim and Burden, 2008). Genotyping was performed by PCR (5'-GAAGCAACCTTTCCTTCCTGAG-3' and 5'-ATTTTCCCTGAGAGCATTGTCC-3'). All experiments were approved by the Animal Care and Use Committee at NYU School of Medicine.

Immunohistochemistry

Diaphragm muscles from adult mice were dissected and fixed for 1.5 h at room temperature in 1% formaldehyde in phosphate buffered saline (PBS). Muscles were washed three times for 15 min in PBS, incubated for 15 min with 0.1M glycine in PBS and rinsed in PBS and 0.5% Triton X-100 (PBT). Muscles were incubated for 1 h in PBT containing 4% normal goat serum (PBTG), and overlaying connective tissue was diligently removed. Axons and nerve terminals were labeled with rabbit polyclonal antibodies against Neurofilament (NF, 1:3000; Synaptic Systems, Goettingen, Germany) and Synapsin (Syn, 1:2000; Synaptic Systems, Goettingen, Germany) overnight at 4° C. in PBTG. After three 1 h washes in PBT, muscles were incubated at 4° C. overnight with Alexa-488 goat anti-rabbit IgG (1:500; Invitrogen) and Alexa-594-conjugated-α-BGT (1:1000 in PBTG; Invitrogen, San Diego, Calif.) to label AChRs. Muscles were washed three times with PBS over 1 h, post fixed (1% formaldehyde in PBS) for 10 min, rinsed in PBS and mounted in Vectashield under a glass coverslip (Vector Labs, Burlingame, Calif.).

Diaphragm muscles from P90 to P160 wild-type (WT), HSA::MuSK-L, SOD1G93A and SOD1G93A; HSA::MuSK-L mice were stained with Alexa-594-conjugated-α-BGT and antibodies to NF and Syn. Confocal images of diaphragm muscles were captured on a Zeiss 510 confocal laser scanning microscope (Carl Zeiss MicroImaging GmbH, Jena, Germany) using a 40× PlanApo objective. Images were compiled into a reconstructed image, and the number of normally innervated, partially innervated and fully denervated synapses was quantified. For each experiment, at least 100 synaptic sites were counted for each genotype, and experiments were performed at least three times.

Survival

To measure longevity, we followed the survival of 300 animals up to 10 months: WT, n=101; HSA::MuSK-L, n=86; SOD1G93A, n=70; and SOD1G93A; HSA::MuSK-L, n=44. Kaplan Meier survival curves were generated with GraphPad Prism software.

Behavioral Tests

Motor function was assessed once per week on a Rota Rod (EZ-Rod 3.05; Accuscan Instruments, Inc., Columbus, Ohio). In each experiment, running performance was measured for at least 6 animals of each genotype from P80 to P160. Mice were placed on a Rota Rod (3.0 cm rotating cylinder) rotating at 1 rpm, and the speed of rotation was gradually increased from 1 to 12 rpm over the course of 40 sec and then maintained at 12 rpm for a maximum of five min. We recorded the time that mice remained on the Rota Rod. Wild-type and HSA::MuSK-L mice routinely ran for the full five min, yielding an assigned value of 100%; the values for other mice were expressed relative to wild-type mice.

Motor fatigue was assessed using an inverted grid hanging test (Kaja et al., 2007). Individual mice were placed in the center of a wire grid, which was mounted 80 cm above a laboratory bench. After gently inverting the grid, we maintained the grid in an inverted position for a maximum of 60 sec and recorded the time that mice remained attached to the grid. Wild-type mice routinely remained attached to the grid for the duration and were assigned a value of 100%; the values for other mice were expressed relative to wild-type mice.

Statistical Analysis

All data are expressed as group means±SEM. For the Kaplan-Meier survival analysis, the log-rank test was used, and survival curves were considered significantly different at $P<0.05$. When appropriate, the one-way ANOVA followed by a Newman-Keuls Multiple Comparison's post-hoc analysis were used to test for differences between samples, and data were considered significantly different at $P<0.05$.

hSOD1 Copy Number Assessment

Figure 6:
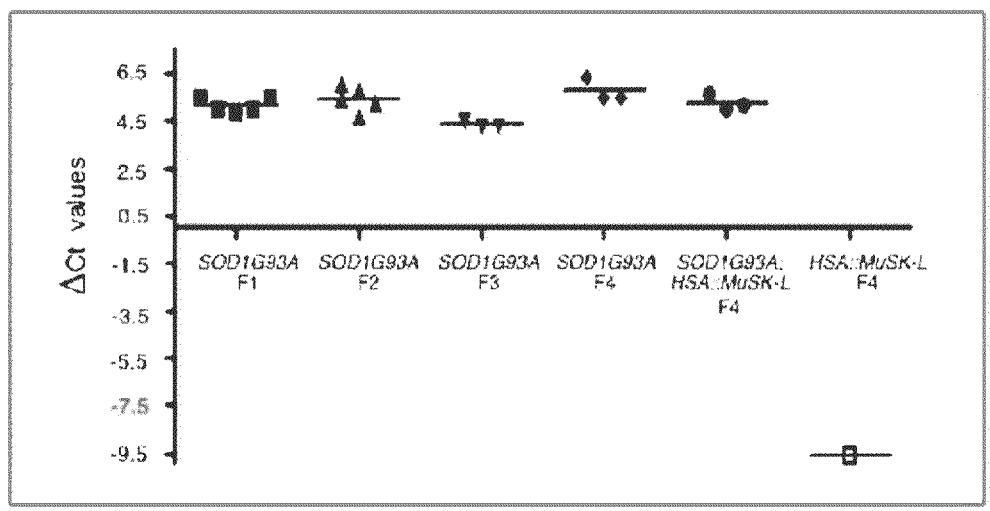
FIG. 6 demonstrates that copy number of the SOD1G93A transgene did not change over multiple generations. The copy number of the SOD1G93A transgene was measured by real time PCR, which revealed that the copy number did not change over multiple generations and during the course of the experiments.

To learn whether SOD1G93A copy number changed during the course of these experiments, copy number was measured using a real time PCR assay. Genomic DNA was extracted from tails using a Qiagen DNA extraction kit (QIAGEN, Valencia, Calif.). Brilliant® II SYBR Green QPCR Master Mix reagent (Stratagene, Santa Clara, Calif.) was used for the real-time amplification of DNA, ranging from 0.15 to 20 ng. Following heating at 50° C. for 2 min and 95° C. for 10 min, DNA was amplified by 40 cycles of 95° C. for 15 sec and 60° C. for 1 min., as suggested by the Jackson Laboratories (Bar Harbor, Me.). We found that the copy number did not change during the course of these experiments (FIG. 6).

Introduction

The withdrawal of motor axons from muscle is the first sign of disease in familial and sporadic forms of ALS, portending a progressive and devastating loss of motor function that culminates in lethal muscle paralysis within five years of diagnosis (Fischer et al., 2004; Pasinelli and Brown, 2006; Schaefer et al., 2005). The mechanisms responsible for axon withdrawal are poorly understood, but the loss of neuromuscular synapses is sufficient to cause muscle paralysis and therefore central to the disease. Although the subsequent loss of motor neurons has received more attention, preventing or delaying motor neuron cell death without preserving neuromuscular synapses cannot stop disease progression. Moreover, studies designed to inhibit motor neuron cell death, either by blocking cell death pathways or providing broadly acting growth factors, have had only a modest impact on disease progression (Kostic et al., 1997; Pun et al., 2006; Sagot et al., 1995).

Dominant mutations in SOD1, TDP-43, FUS, and the recently discovered C9orf72 gene are responsible for familial forms of ALS and together represent ~17% of all cases of ALS (Chen-Plotkin et al., 2010; Kwiatkowski et al., 2009; Majounie et al., 2012; Pasinelli and Brown, 2006; Renton et al., 2011; Vance et al., 2009). The pathological hallmarks of the disease are well replicated in mice that overexpress mutant forms of SOD1 in motor neurons, providing an excellent model system for studying the pathology of ALS and identifying approaches to treat this devastating disease (Pasinelli and Brown, 2006). Although cell types other than motor neurons, including grey matter oligodendrocytes and microglia contribute to disease onset and progression (Ilieva et al., 2009; Kang et al., 2010), dominant mutations in SOD1 act largely in an autonomous manner within motor neurons, consistent with the idea that ALS is primarily, though not entirely, a disease of upper and lower motor neurons.

Skeletal muscles provide retrograde signals that promote the differentiation and stabilization of motor nerve terminals (Burden, 1998; Sanes and Lichtman, 2001). In the absence of these muscle-derived retrograde signals, developing motor axons grow aimlessly within muscle and fail to form synapses. The production of muscle-derived retrograde signals depends upon a synaptic receptor tyrosine kinase, termed MuSK, and Lrp4, a receptor for Agrin that forms a complex with MuSK (DeChiara et al., 1996; Kim et al., 2008; Weatherbee et al., 2006; Zhang et al., 2008). During normal development, Lrp4/MuSK signaling initiates neuromuscular synapse formation, whereas the subsequent stabilization of nascent synapses also requires neuronal Agrin, which binds to Lrp4 and strongly stimulates MuSK (Kim and Burden, 2008; Zhang et al., 2008; Zhang et al., 2011). In the absence of Agrin, neuromuscular synapses form, but motor axon terminals subsequently withdraw, leading to defective neuromuscular transmission and perinatal death (Gautam et al., 1996; Lin et al., 2001; Lin et al., 2005; Misgeld et al., 2005). Retrograde signaling also regulates the stability and maintenance of synapses in adult animals, as interfering with MuSK function in adult mice causes disassembly of neuromuscular synapses (Hesser et al., 2006; Kong et al., 2004). Because a failure to maintain neuromuscular synapses is central to all forms of ALS, we tested whether increasing retrograde signaling in SOD1 transgenic mice could stabilize neuromuscular synapses, delay axon withdrawal and ameliorate the symptoms of disease.

Results

Previously, we found that a modest (three-fold) increase in MuSK expression is sufficient to maintain neuromuscular synapses in agrin mutant mice, thereby preventing perinatal lethality and promoting postnatal survival (Kim and Burden, 2008). We therefore wondered whether increasing MuSK expression in a mouse model of ALS would stabilize neuromuscular synapses, delay motor axon withdrawal, and increase muscle function.

To investigate this issue, we crossed HSA::MuSK-L mice, which express three-fold more MuSK than wild-type mice, with SOD1G93A mice, and used histological assays to compare the rate and extent of denervation of SOD1G93A and MuSK-L; SOD1G93A mice. We stained whole mounts of the diaphragm muscle with antibodies against Synapsin to label nerve terminals and with α-bungarotoxin (α-BGT) to visualize acetylcholine receptors (AChRs) in muscle. In wild-type and MuSK-L transgenic mice, nerve terminals are apposed to AChRs, and the coincidence of Synapsin/AChR staining defines innervated synaptic sites (FIG. 1). In SOD1G93A mice, axons from fast, fatigable motor neurons withdraw early in disease (Pun et al., 2006). Axons from slow, non-fatigable motor neurons are lost more slowly and compensate by sprouting and temporarily reoccupying denervated synaptic sites on fast myofibers (Pun et al., 2006). We first measured the number of synaptic sites that lacked Synapsin staining and were therefore completely denervated. In SOD1G93A mice, denervation of the diaphragm muscle became evident at P120, and the extent of denervation increased gradually over the next 20 days, reaching a maximum of ~50% at P140 (FIG. 1), similar to the time course and extent of denervation observed in other muscles (Schaefer et al., 2005). In contrast, in SOD1G93A mice over-expressing MuSK, denervation of the diaphragm muscle began ten days later, and the extent of denervation remained less than 10% through P150 (FIG. 1).

Figure 5:
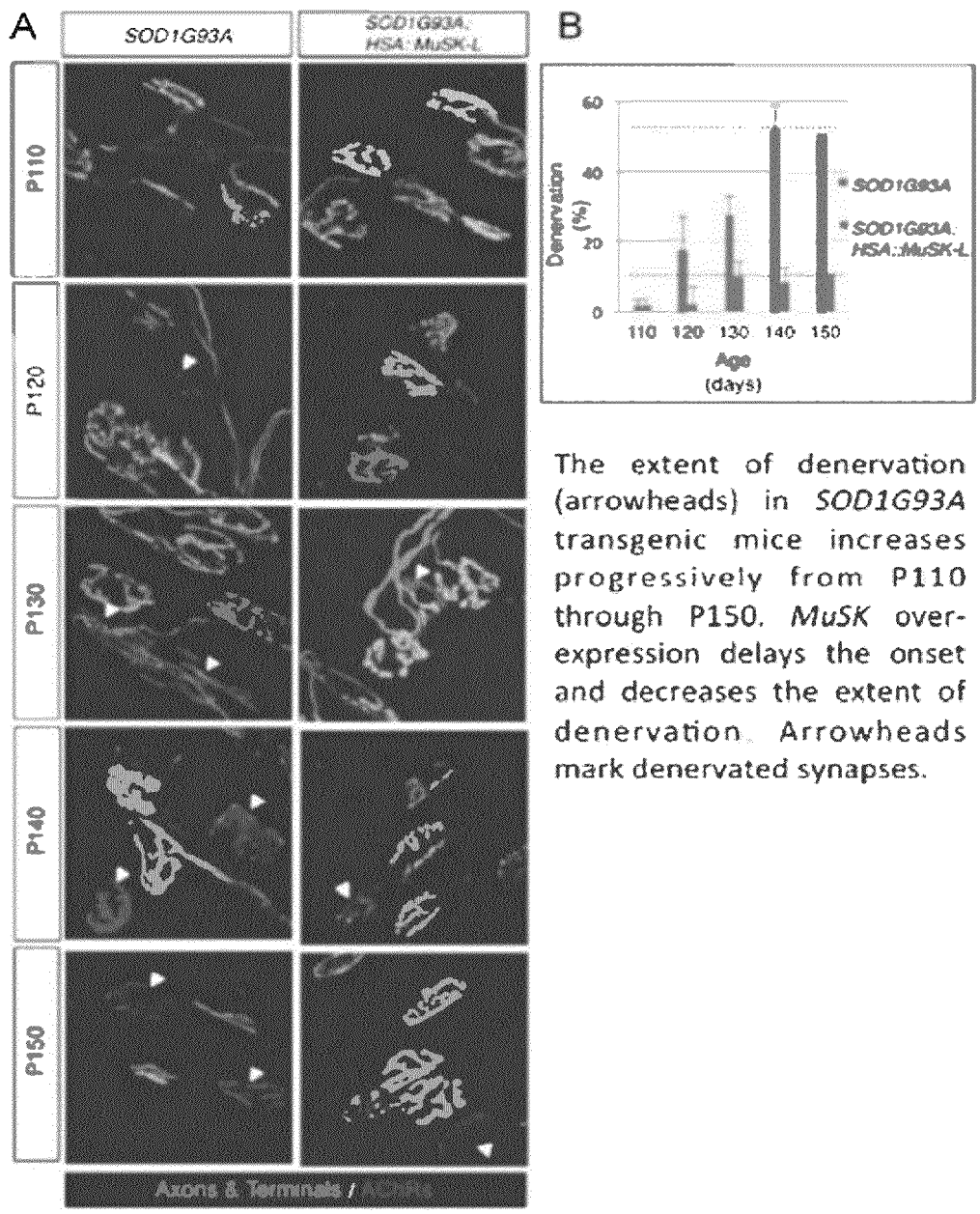
FIG. 5 shows that MuSK over-expression delays the onset and reduces the extent of denervation in SOD1G93A mice. A) Immunohistochemistry of the diaphragm muscle stained with antibodies against Synapsin to label nerve terminals and with α-bungarotoxin (α-BGT) to visualize acetylcholine receptors (AChRs) in muscle is shown. The extent of denervation (arrowheads) in SOD1G93A transgenic mice increases progressively from P110 through P150. MuSK over-expression delays the onset and decreases the extent of denervation in SOD1G93A; HAS::MuSK-L transgenic mice. Arrowhead mark denervated synapses. B) Histogram depicting % denervation relative to age.

By P160, the extent of denervation increased and approached the level found in SOD1G93A mice (FIGS. 1, 5). These findings indicate that MuSK over-expression protected synapses in SOD1G93A mice from denervation by delaying the onset and decreasing the extent of denervation for over 40 days.

Figure 2:
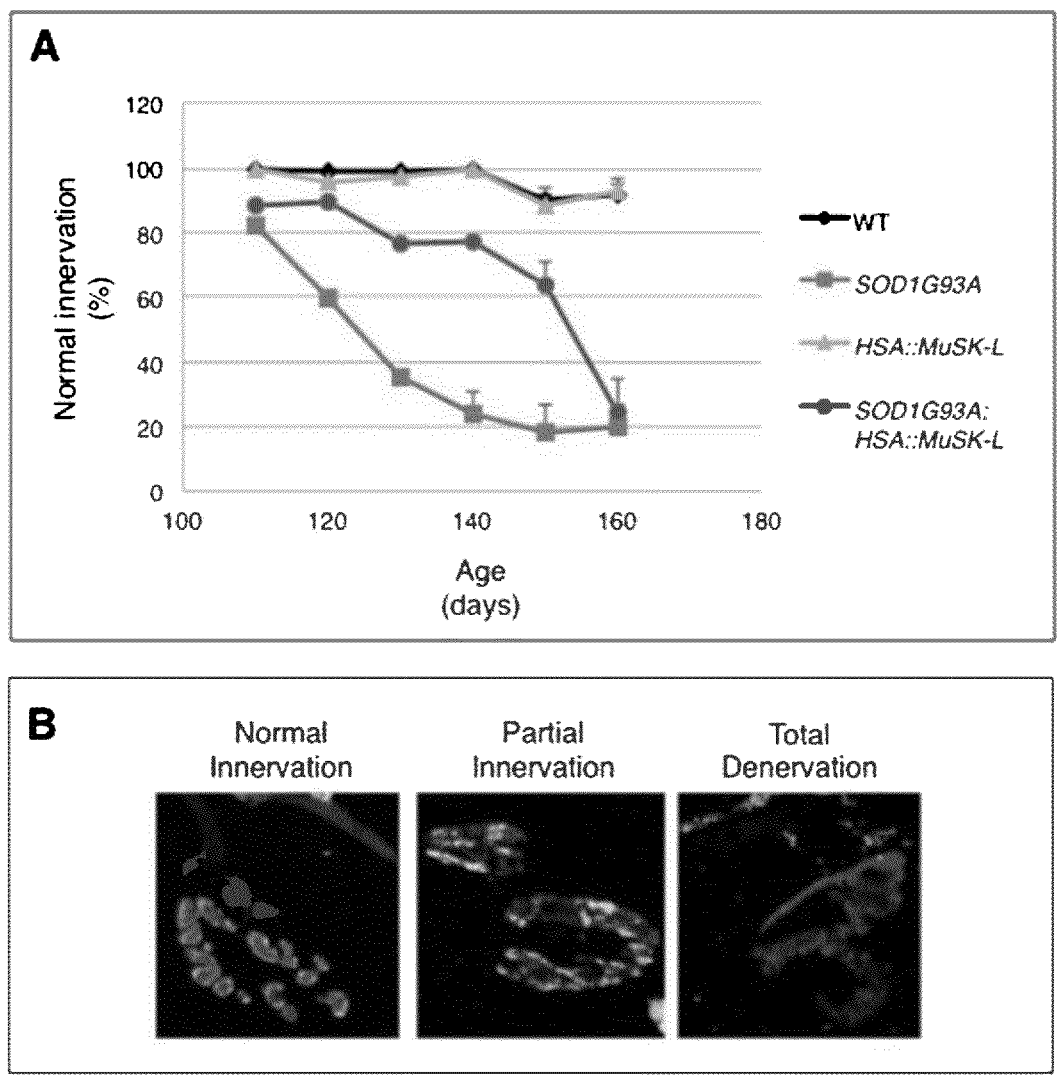
FIG. 2 shows that MuSK over-expression preserves full innervation in SOD1G93A mice. A) In SOD1G93A mice, the number of normally innervated synapses falls to 20% by P140. In SOD1G93A mice over-expressing MuSK, nearly 80% of synapses remain normally innervated at P140. B) Normally innervated, partially innervated and denervated synapses are distinguished by differences in overlap of staining for Synapsin and AChRs.

The remaining synapses included normally and partially innervated synapses. At partially innervated synapses, Synapsin staining incompletely overlapped the AChR-rich postsynaptic membrane, leaving patches of the postsynaptic membrane devoid of innervation (FIG. 2). To determine whether MuSK expression preserved normal innervation, we measured the number of synaptic sites that were normally innervated. FIG. 2 shows that the number of normally innervated synapses fell dramatically after P110 in SOD1G93A mice, reaching a plateau of 20% at P140. MuSK over-expression in SOD1G93A mice preserved normal innervation: the fall in normal innervation was delayed, and >60% of synapses remained normally innervated as late as P150. These findings show that MuSK over-expression preserves normally innervated synapses in SOD1G93A mice for over 40 days. MuSK over-expression may preserve innervation by delaying denervation, increasing reinnervation or both.

Figure 3:
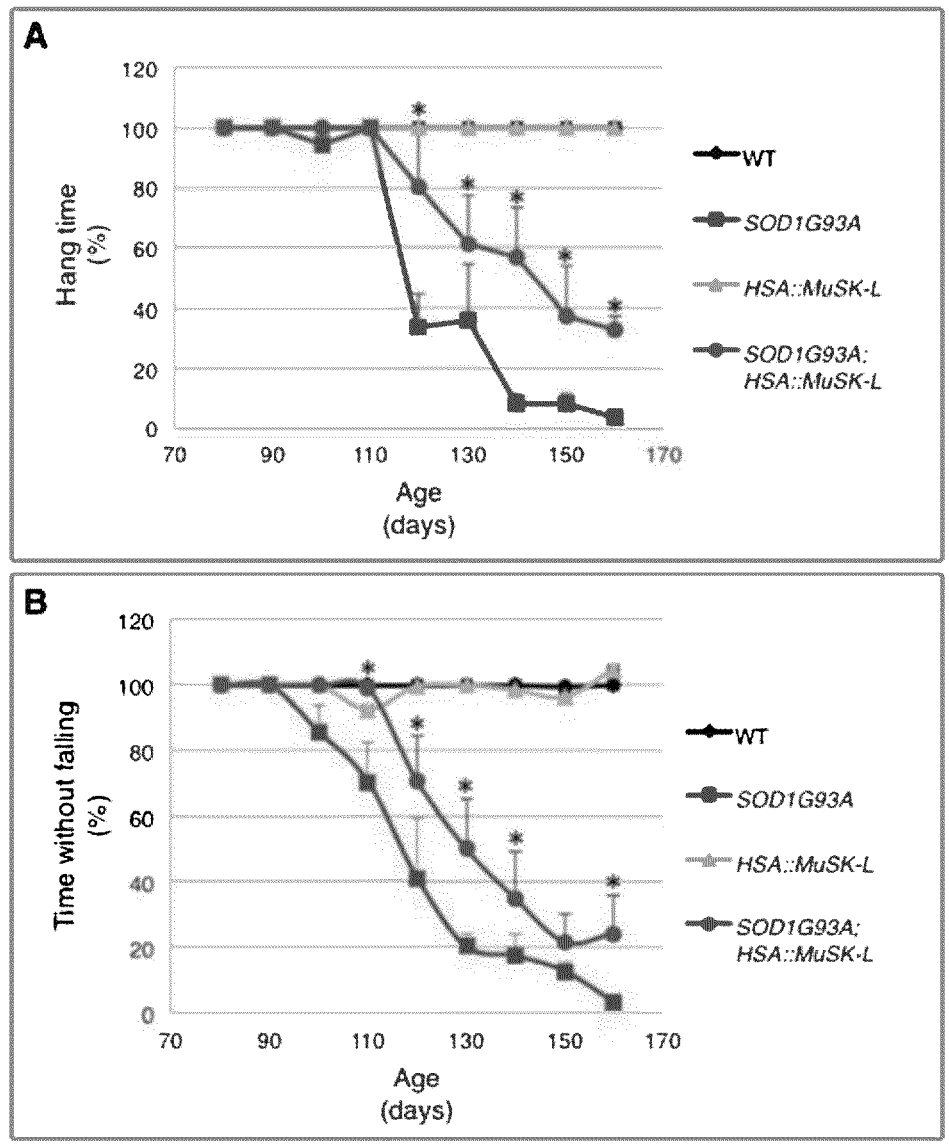
FIG. 3 shows that grip strength and Rota Rod performance are enhanced in SOD1G93A mice over-expressing MuSK. A) The ability of SOD1G93A mice to cling to the wire grid declines rapidly after P110. MuSK over-expression increases the time that mice cling to the wire grid. B) SOD1G93A mice fall from the Rota Rod beginning at P100 whereas mice over-expressing MuSK begin to fall at P120. SOD1G93A mice over-expressing MuSK remain on the rotating bar longer than SOD1G93A mice at all subsequent times. The analysis included 25-30 mice at P80-P120, 35 mice at P130, 40 mice at P140, 32 mice at P150 and 32 at P160. Significantly different values ($p<0.05$) for SOD1G93A and SOD1G93A; HSA::MuSK-L mice are indicated (*).
Figure 4:
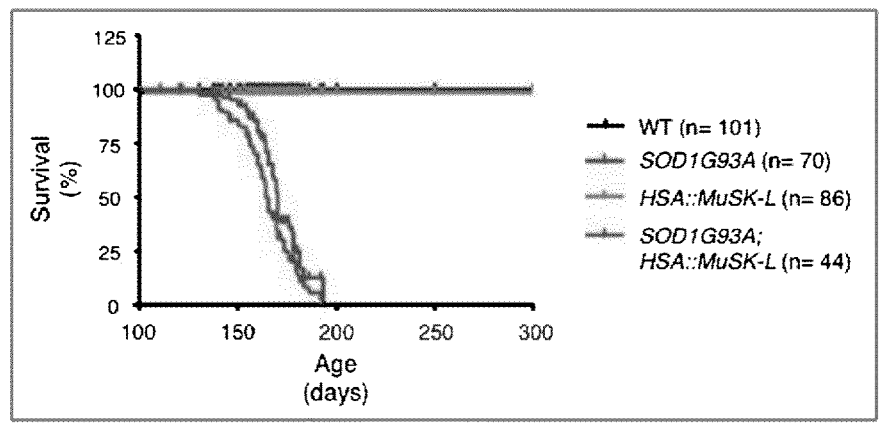
FIG. 4 shows that MuSK over-expression does not increase longevity of SOD1G93A mice. A) The mean survival of SOD1G93A; HSA::MuSK-L mice was 164.82±1.83 days, which is not significantly longer ($p>0.05$) than SOD1G93A mice (160.1±2.09 days). B) Model for stabilizing motor nerve terminals. In SOD1G93A mice, synapses become denervated as motor neurons lose expression of receptors for muscle retrograde signals, which promote differentiation and muscle-attachment of nerve terminals. In SOD1G93A mice over-expressing MuSK, retrograde signaling is enhanced, preserving nerve terminal differentiation and muscle-attachment at times when receptor expression is reduced but not absent.
Figure 4:
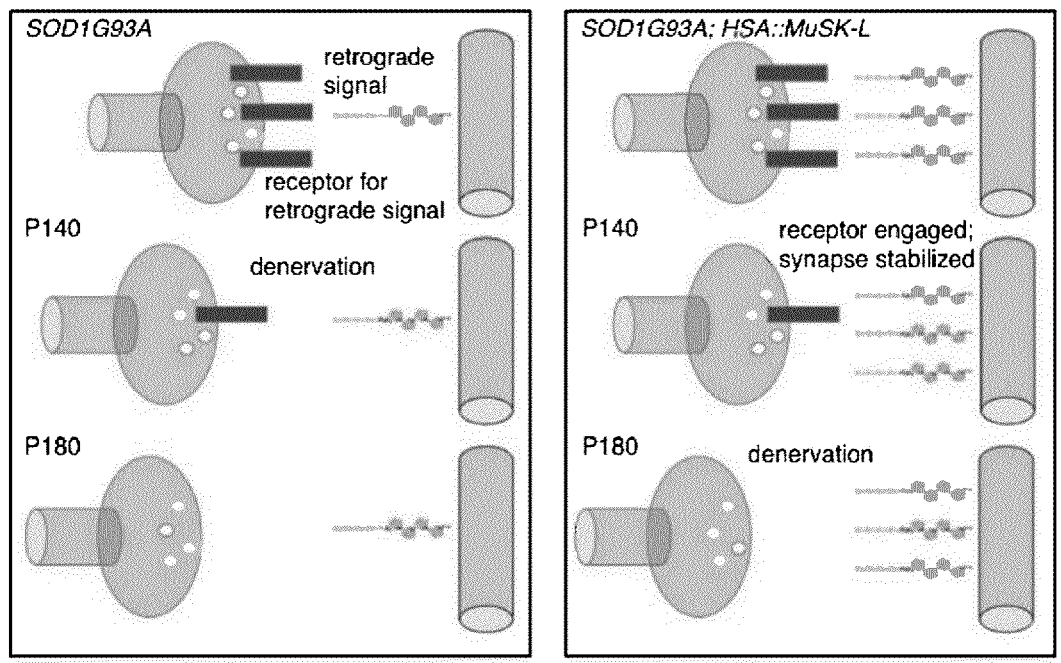

To determine whether the delay in onset and decrease in extent of denervation were accompanied by improved motor function, we used a Rota Rod and an inverted grid hanging test to measure the motor performance of SOD1G93A and MuSK-L; SOD1G93A mice. FIG. 3 shows that MuSK-L; SOD1G93A mice out-performed SOD1G93A mice in both tests of motor function. MuSK-L; SOD1G93A mice clung to the inverted grid longer than SOD1G93A mice, beginning at P120 and continuing through P160, the last time point that we measured. Although the motor function of MuSK-L; SOD1G93A mice declined over time, SOD1G93A mice over-expressing MuSK out-performed SOD1G93A mice by 2-3 fold at P120 and P130 and by 5-9 fold from P140 through P160 (FIG. 3a). Likewise, MuSK-L; SOD1G93A mice out-performed SOD1G93A mice on the Rota Rod from P100 through P160 (FIG. 3b). Moreover, these differences in motor behavior were evident simply by monitoring the mobility of mice in their housing. Nonetheless, the benefit from MuSK over-expression is not enduring, since the eventual withdrawal of nerve terminals and decrease in motor function leads to death at a time similar to SOD1G93A mice (FIG. 4a).

Discussion

Results presented herein reveal that a modest increase in MuSK expression is sufficient to maintain neuromuscular synapses in SOD1G93A mice, delaying muscle denervation and improving muscle function for over 30 days. These findings indicate that the loss of motor nerve terminals can be delayed by co-opting a retrograde signaling pathway that normally functions to stimulate the differentiation and stabilization of these terminals. As such, our findings suggest a novel therapeutic approach to slow the steady decline in muscle strength and motor function in ALS. Moreover, because motor axon withdrawal is an early, characteristic and critical feature of disease in all forms of ALS, we expect that increasing MuSK activity might provide benefit in both familial and sporadic forms of ALS.

The benefit from MuSK over-expression is not permanent. The eventual withdrawal of nerve terminals and loss of motor function indicate that motor neurons ultimately become sufficiently compromised that motor terminals can no longer be stabilized by increasing MuSK signaling from muscle, suggesting that the terminals eventually lose their ability to respond to critical MuSK-dependent muscle-derived signals. Our recent studies demonstrate that Lrp4 is a critical muscle-derived retrograde signal that acts bi-directionally to coordinate presynaptic and postsynaptic differentiation (Yumoto et al., Nature, DOI 10.1038/nature11348). A failure to transport the Lrp4 receptor, or components that act downstream from this receptor, within motor axons may ultimately render motor neurons unresponsive to retrograde signaling (FIG. 4b). Identification of the Lrp4 receptor might provide additional targets that can be manipulated to strengthen and prolong the response of compromised motor neurons. Alternatively, the eventual withdrawal of nerve terminals could be caused by the death of motor neurons, a late event in ALS that becomes apparent in SOD1G93A mice one to two months after denervation has reached a plateau (Fischer et al., 2004). If so, combining other therapies, aimed to promote motor neuron survival, with an increase in MuSK activity may lengthen the duration of benefit.

Like other receptor tyrosine kinases, tyrosine phosphorylation and activation of MuSK depend upon MuSK dimerization (Stiegler et al., 2009), which is stimulated by binding of Agrin to Lrp4 (Zhang et al., 2011). MuSK over-expression is sufficient to promote MuSK dimerization and increase MuSK kinase activity (Watty et al., 2000). It will be necessary, however, to find alternatives to MuSK over-expression to activate MuSK in vivo. Soluble forms of neuronal Agrin or Lrp4 may stimulate MuSK in vivo (Zhang et al., 2011), or a screen for small molecule activators of MuSK may identify new agonists. Human single chain variable region antibodies (ScFv) to MuSK have also been shown to stimulate MuSK tyrosine phosphorylation and AChR clustering in cultured myotubes (Xie et al., 1997). The mechanisms by which these agonist antibodies stimulate MuSK are poorly understood, but these antibodies may provide an alternative means to activate MuSK in vivo, an approach that we are currently investigating.

Example II

Further to the above findings, the present inventor is investigating whether proven agonist antibodies to MuSK stimulate MuSK phosphorylation in vivo and likewise improve motor function in ALS mice.

As indicated herein above, previous studies have shown that agonist antibodies to MuSK stimulate MuSK phosphorylation in cultured myotubes (Xie et al., 1997). To explore the properties of these agonist antibodies to MuSK within the context of the present disclosure, an exemplary one of these antibodies, agonist antibody #13 of Xie et al. (1997), will be evaluated. Xie et al. describe agonist antibody, #13, as the most potent of these antibodies. Accordingly, agonist antibody #13 will be assessed to determine if this antibody stimulates MuSK phosphorylation in mice. Because ScFv and truncated (Fab) antibodies have short (1-2 hr) half-lives in vivo, corresponding full length IgG molecules that are deficient in effector functions (e.g., complement activation) will also be assessed. Protocols for mutating IgG to ablate effector function are known in the art as exemplified by Armour et al. (1999) and Shields et al. (2001), the entire content of each of which is incorporated herein in its entirety. Moreover, because the current version of antibody #13 includes a human constant region, the human heavy chain sequence contained in these antibodies will be exchanged with a murine heavy chain sequence to avoid generating an immune response in mice receiving injections for a month or longer. Using such protocols, the optimal dose, frequency and route of delivery for an agonist antibody can be determined. These experiments will establish a protocol for activating MuSK in vivo, which information will provide additional guidance with respect to therapeutic applications of these agonist antibodies and the like.

More particularly, antibodies will be injected into wild-type mice at P100 and MuSK phosphorylation will be measured two, four or six days later. Additional time points may, moreover, be added. The antibodies will be injected into the peritoneum (IP) or intravenously (IV), and the dose will be varied from 0.1 mg/kg to 10 mg/kg. At the outset, IgG molecules will be injected that are defective in effector function, due to mutations in the lower hinge region that impair binding to Fcγ receptors (Armour et al., 1999; Shields et al., 2001), or by substituting the constant region from human IgG4 (or mouse IgG1), which inefficiently engages complement (Aalberse and Schuurman, 2002). These experiments will establish the optimal route for antibody delivery and the relationship between the amount of injected antibody and the level of MuSK phosphorylation. Moreover, these experiments will provide information as to the time required for the agonist antibody to activate MuSK following a single injection and the persistence of MuSK phosphorylation following a single injection.

MuSK phosphorylation can be measured, for example, by immunoprecipitating MuSK from cell lysates of dissected tibialis anterior, diaphragm or gastrocnemius muscles and probing Western blots for MuSK or tyrosine phosphorylation, as previously described (Friese et al., 2007; Hallock et al., 2010; Herbst and Burden, 2000).

The above procedure can, furthermore, be modified by adding a second injection to evaluate whether the effects of repeated injections are predictably additive. It is unclear, for example, whether divalent, agonist IgG antibodies to MuSK down-regulate MuSK surface expression. Receptor down-regulation is likely to impact responsiveness to repeated injections. In one set of experiments, cultured myotubes will be treated with an agonist antibody and MuSK surface expression measured, as described previously (Stiegler et al. J Mol Biol 2006 364(3):424-433, the entire content of which is incorporated herein by reference). In addition, by injecting the agonist antibody a second time (or multiple times) in vivo, one or two weeks following the first injection, an assessment of whether the response to the agonist antibody has been attenuated, as would be expected if the first antibody treatment led to down regulation of MuSK surface expression, can be performed. Together, this knowledge will direct further experiments to establish how often injections will be required to achieve an adequate level of MuSK phosphorylation during the 40 to 80 day period required to determine whether the agonist antibody decreases muscle denervation and improves motor behavior, as described herein above.

Once optimal dosing, frequency and route of delivery for the agonist antibody are established, agonist antibody or a control antibody will be injected into SOD1G93A mice, beginning at P100, prior to the onset of muscle denervation and motor dysfunction, and injections will be continued through P140, when muscle denervation and motor dysfunction have reached peak levels. During this time frame, histological and behavioral assays can be performed as described herein above to make a determination as to whether the agonist antibody delays the onset and extent of denervation, as well as improves motor behavior in SOD1G93A mice.

To determine whether the agonist antibody slows disease progression when injected after the onset of disease symptoms, antibody injections can be commenced at P120, after muscle denervation and motor dysfunction in SOD1G93A mice are well apparent and at ~one-half their peak values. As shown herein above, the extent of muscle denervation reaches ~one-half the peak value by P120 and motor dysfunction has likewise deteriorated to a similar extent by this age. See, for example, FIG. 1. In view of the above, agonist antibody injections will commence at P120 and muscle denervation and motor dysfunction will be assessed at P140. These experiments will reveal the ability of an agonist antibody tested to slow, halt or reverse disease progression.

The prolonged impact of an agonist antibody on disease, reducing denervation, improving motor function and prolonging survival beyond P140 can, moreover, be assessed by continuing antibody injections from P140 to P180. As described above, a modest increase in MuSK expression delayed the onset and decreased the extent of muscle denervation, improving motor behavior up to P150. By P160, however, denervation was similar in SOD1G93A mice over-expressing MuSK and SOD1G93A mice, and survival was not significantly prolonged. Nonetheless, it is possible that activating MuSK with the agonist antibody may prevent denervation for a longer period of time and prolong survival. To explore this potentiality, the ability of agonist antibody to alter the extent of denervation at P180 and prolong survival will also be assessed by continuing injections from P140 to P180.

Upon establishing that an agonist antibody improves motor function in ALS mice, assessments of these antibodies will be performed in a clinical setting to determine therapeutic efficacy of the antibodies in human subjects.

Figure 7:
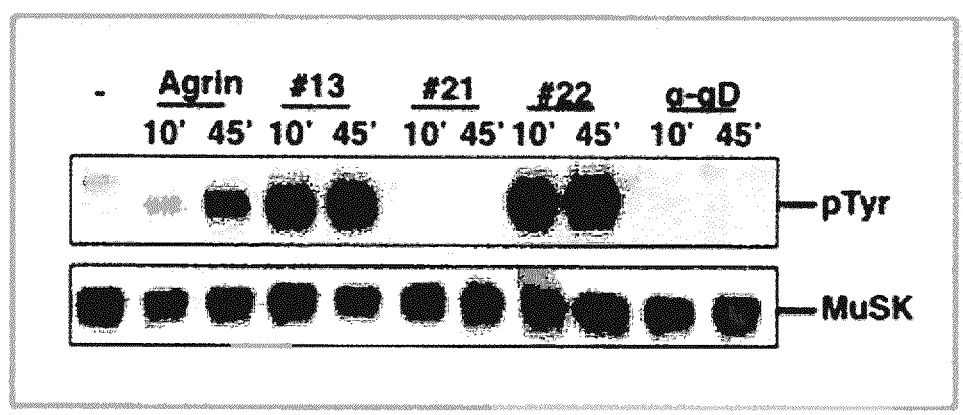
FIG. 7 reveals that MuSK agonist antibodies #13 and #22 stimulate MuSK phosphorylation. Antibody #22, which reacts with MuSK, and a negative control antibody (g-gD) fail to stimulate MuSK. C2 myotubes were treated with Agrin (1 nM) or antibodies to MuSK (50 nM) for the indicated times. MuSK was immunoprecipitated from lysates, and Western blots were probed with rabbit antibodies to MuSK or phosphotyrosine, as described previously (Friese et al., 2007; Hallock et al., 2010; Herbst and Burden, 2000, the entire content of each of which is incorporated herein by reference).

In proof of principle experiments, cDNAs encoding three antibodies to MuSK were re-synthesized, two of which were reported by Xie et al. (1997) to function as agonist antibodies, whereas the third was determined to bind to MuSK, but failed to stimulate MuSK. These three antibodies, as well as an additional negative control antibody (all of which were synthesized as IgG molecules) were tested to determine if they recognize mouse and human MuSK using an ELISA. These antibodies were also tested to assess their ability to stimulate MuSK phosphorylation when added to cultured mouse myotubes. As shown in FIG. 7, the agonist antibodies do indeed stimulate robust MuSK phosphorylation. The negative control antibody, as well as another antibody that binds MuSK, failed to stimulate MuSK phosphorylation. Given these findings, the properties of two agonist antibodies, #13 and #22, to MuSK have been confirmed in vitro and have thus set the stage for the above-outlined in vivo experiments. The in vitro studies also revealed that the agonist antibodies react with mouse and human MuSK, although there is a slight preference for human MuSK.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

Various references are cited throughout this Specification, each of which is incorporated herein by reference in its entirety.

REFERENCES

Aalberse, R. C., and Schuurman, J. (2002). IgG4 breaking the rules. Immunology 105, 9-19.

Armour, K. L., Clark, M. R., Hadley, A. G., and Williamson, L. M. (1999). Recombinant human IgG molecules lacking Fcgamma receptor I binding and monocyte triggering activities. European journal of immunology 29, 2613-2624.

Burden, S. J. (1998). The formation of neuromuscular synapses. Genes Dev 12, 133-148.

Chen-Plotkin, A. S., Lee, V. M., and Trojanowski, J. Q. (2010). TAR DNA-binding protein 43 in neurodegenerative disease. Nature reviews Neurology 6, 211-220.

DeChiara, T. M., Bowen, D. C., Valenzuela, D. M., Simmons, M. V., Poueymirou, W. T., Thomas, S., Kinetz, E., Compton, D. L., Rojas, E., Park, J. S., et al. (1996). The receptor tyrosine kinase MuSK is required for neuromuscular junction formation in vivo. Cell 85, 501-512.

Fischer, L. R., Culver, D. G., Tennant, P., Davis, A. A., Wang, M., Castellano-Sanchez, A., Khan, J., Polak, M. A., and Glass, J. D. (2004). Amyotrophic lateral sclerosis is a distal axonopathy: evidence in mice and man. Experimental neurology 185, 232-240.

Friese, M. B., Blagden, C. S., and Burden, S. J. (2007). Synaptic differentiation is defective in mice lacking acetylcholine receptor beta-subunit tyrosine phosphorylation. Development 134, 4167-4176.

Gautam, M., Noakes, P. G., Moscoso, L., Rupp, F., Scheller, R. H., Merlie, J. P., and Sanes, J. R. (1996). Defective neuromuscular synaptogenesis in agrin-deficient mutant mice. Cell 85, 525-535.

Hallock, P. T., Xu, C. F., Park, T. J., Neubert, T. A., Curran, T., and Burden, S. J. (2010). Dok-7 regulates neuromuscular synapse formation by recruiting Crk and Crk-L. Genes Dev 24, 2451-2461.

Herbst, R., and Burden, S. J. (2000). The juxtamembrane region of MuSK has a critical role in agrin-mediated signaling. The EMBO journal 19, 67-77.

Hesser, B. A., Henschel, O., and Witzemann, V. (2006). Synapse disassembly and formation of new synapses in postnatal muscle upon conditional inactivation of MuSK. Molecular and cellular neurosciences 31, 470-480.

Ilieva, H., Polymenidou, M., and Cleveland, D. W. (2009). Non-cell autonomous toxicity in neurodegenerative disorders: ALS and beyond. The Journal of cell biology 187, 761-772.

Kaja, S., van de Ven, R. C., van Dijk, J. G., Verschuuren, J. J., Arahata, K., Frants, R. R., Ferrari, M. D., van den Maagdenberg, A. M., and Plomp, J. J. (2007). Severely impaired neuromuscular synaptic transmission causes muscle weakness in the Cacna1a-mutant mouse rolling Nagoya. The European journal of neuroscience 25, 2009-2020.

Kang, S. H., Fukaya, M., Yang, J. K., Rothstein, J. D., and Bergles, D. E. (2010). NG2+ CNS glial progenitors remain committed to the oligodendrocyte lineage in postnatal life and following neurodegeneration. Neuron 68, 668-681.

Kim, N., and Burden, S. J. (2008). MuSK controls where motor axons grow and form synapses. Nature neuroscience 11, 19-27.

Kim, N., Stiegler, A. L., Cameron, T. O., Hallock, P. T., Gomez, A M., Huang, J. H., Hubbard, S. R., Dustin, M. L., and Burden, S. J. (2008). Lrp4 is a receptor for Agrin and forms a complex with MuSK Cell 135, 334-342.

Kong, X. C., Barzaghi, P., and Ruegg, M. A. (2004). Inhibition of synapse assembly in mammalian muscle in vivo by RNA interference. EMBO reports 5, 183-188.

Kostic, V., Jackson-Lewis, V., de Bilbao, F., Dubois-Dauphin, M., and Przedborski, S. (1997). Bcl-2: prolonging life in a transgenic mouse model of familial amyotrophic lateral sclerosis. Science 277, 559-562.

Kwiatkowski, T. J., Jr., Bosco, D. A., Leclerc, A. L., Tamrazian, E., Vanderburg, C. R., Russ, C., Davis, A., Gilchrist, J., Kasarskis, E. J., Munsat, T., et al. (2009). Mutations in the FUS/TLS gene on chromosome 16 cause familial amyotrophic lateral sclerosis. Science 323, 1205-1208.

Lin, W., Burgess, R. W., Dominguez, B., Pfaff, S. L., Sanes, J. R., and Lee, K. F. (2001). Distinct roles of nerve and muscle in postsynaptic differentiation of the neuromuscular synapse. Nature 410, 1057-1064.

Lin, W., Dominguez, B., Yang, J., Aryal, P., Brandon, E. P., Gage, F. H., and Lee, K. F. (2005). Neurotransmitter acetylcholine negatively regulates neuromuscular synapse formation by a CdkS-dependent mechanism. Neuron 46, 569-579.

Majounie, E., Renton, A. E., Mok, K., Dopper, E. G., Waite, A., Rollinson, S., Chio, A., Restagno, G., Nicolaou, N., Simon-Sanchez, J., et al. (2012). Frequency of the C9orf72 hexanucleotide repeat expansion in patients with amyotrophic lateral sclerosis and frontotemporal dementia: a cross-sectional study. Lancet neurology 11, 323-330.

Miller et al. (2006). Gene transfer demonstrates that muscle is not a primary target for non-cell-autonomous toxicity in familial amyotrophic lateral sclerosis. Proceedings of the National Academy of Sciences of the United States of America 103, 19546-19551.

Misgeld, T., Kummer, T. T., Lichtman, J. W., and Sanes, J. R. (2005). Agrin promotes synaptic differentiation by counteracting an inhibitory effect of neurotransmitter. Proceedings of the National Academy of Sciences of the United States of America 102, 11088-11093.

Pasinelli, P., and Brown, R. H. (2006). Molecular biology of amyotrophic lateral sclerosis: insights from genetics. Nature reviews Neuroscience 7, 710-723.

Pun, S., Santos, A. F., Saxena, S., Xu, L., and Caroni, P. (2006). Selective vulnerability and pruning of phasic motoneuron axons in motoneuron disease alleviated by CNTF. Nature neuroscience 9, 408-419.

Renton, A. E., Majounie, E., Waite, A., Simon-Sanchez, J., Rollinson, S., Gibbs, J. R., Schymick, J. C., Laaksovirta, H., van Swieten, J. C., Myllykangas, L., et al. (2011). A hexanucleotide repeat expansion in C9ORF72 is the cause of chromosome 9p21-linked ALS-FTD. Neuron 72, 257-268.

Sagot, Y., Dubois-Dauphin, M., Tan, S. A., de Bilbao, F., Aebischer, P., Martinou, J. C., and Kato, A. C. (1995). Bcl-2 overexpression prevents motoneuron cell body loss but not axonal degeneration in a mouse model of a neurodegenerative disease. The Journal of neuroscience: the official journal of the Society for Neuroscience 15, 7727-7733.

Sanes, J. R., and Lichtman, J. W. (2001). Induction, assembly, maturation and maintenance of a postsynaptic apparatus. Nature reviews Neuroscience 2, 791-805.

Schaefer, A M., Sanes, J. R., and Lichtman, J. W. (2005). A compensatory subpopulation of motor neurons in a mouse model of amyotrophic lateral sclerosis. The Journal of comparative neurology 490, 209-219.

Shields, R. L., Namenuk, A. K., Hong, K., Meng, Y. G., Rae, J., Briggs, J., Xie, D., Lai, J., Stadlen, A., Li, B., et al. (2001). High resolution mapping of the binding site on human IgG1 for Fc gamma RI, Fc gamma RII, Fc gamma RIII, and FcRn and design of IgG1 variants with improved binding to the Fc gamma R. The Journal of biological chemistry 276, 6591-6604.

Stiegler, A. L., Burden, S. J., and Hubbard, S. R. (2009). Crystal structure of the frizzled-like cysteine-rich domain of the receptor tyrosine kinase MuSK. Journal of molecular biology 393, 1-9.

Vance, C., Rogelj, B., Hortobagyi, T., De Vos, K. J., Nishimura, A. L., Sreedharan, J., Hu, X., Smith, B., Ruddy, D., Wright, P., et al. (2009). Mutations in FUS, an RNA processing protein, cause familial amyotrophic lateral sclerosis type 6. Science 323, 1208-1211.

Watty, A., Neubauer, G., Dreger, M., Zimmer, M., Wilm, M., and Burden, S. J. (2000). The in vitro and in vivo phosphotyrosine map of activated MuSK. Proceedings of the National Academy of Sciences of the United States of America 97, 4585-4590.

Weatherbee, S. D., Anderson, K. V., and Niswander, L. A. (2006). LDL-receptor-related protein 4 is crucial for formation of the neuromuscular junction. Development 133, 4993-5000.

Xie, M. H., Yuan, J., Adams, C., and Gurney, A. (1997). Direct demonstration of MuSK involvement in acetylcholine receptor clustering through identification of agonist ScFv. Nature biotechnology 15, 768-771.

Zhang, B., Luo, S., Wang, Q., Suzuki, T., Xiong, W. C., and Mei, L. (2008). LRP4 serves as a coreceptor of agrin. Neuron 60, 285-297.

Zhang, W., Coldefy, A. S., Hubbard, S. R., and Burden, S. J. (2011). Agrin binds to the N-terminal region of Lrp4 protein and stimulates association between Lrp4 and the first immunoglobulin-like domain in muscle-specific kinase (MuSK). The Journal of biological chemistry 286, 40624-40630.

What is claimed is:

1. A method for delaying motor dysfunction in a subject suffering from amyotrophic lateral sclerosis (ALS), the method comprising the steps of: selecting the subject suffering from ALS and administering an agent that increases muscle specific receptor kinase (MuSK) activity to the subject in a therapeutically effective amount sufficient to increase MuSK activity in the subject, wherein the agent is an antibody or antibody fragment that increases MuSK activity upon binding to MuSK, thereby improving motor function in the subject.

2. A method for preserving neuromuscular synapses in a subject suffering from amyotrophic lateral sclerosis (ALS), the method comprising the steps of: selecting the subject suffering from ALS and administering an agent that increases muscle specific receptor kinase (MuSK) activity to the subject in a therapeutically effective amount sufficient to increase MuSK activity in the subject, wherein the agent is an antibody or antibody fragment that increases MuSK activity upon binding to MuSK, thereby preserving neuromuscular synapses in the subject.

3. The method of claim 1, wherein the delay in motor dysfunction is measurable by determining innervation levels.

4. The method of claim 1, wherein administering the agent maintains innervation levels in the subject.

5. The method of claim 1, wherein administering the agent stabilizes motor axon synapses or increases the number of motor axon synapses in the subject.

6. The method of claim 1, wherein the subject is a mouse comprising a transgene with a mutation in superoxide dismutase (SOD1).

7. The method of claim 6, wherein the mouse comprises a transgene with a mutation in SOD1, wherein the transgene is SOD1G93A.

8. The method of claim 1, wherein the subject is a human.

* * * * *

```
                               SEQUENCE LISTING

<160> NUMBER OF SEQ ID NOS: 4

<210> SEQ ID NO 1
<211> LENGTH: 7343
<212> TYPE: DNA
<213> ORGANISM: Homo sapiens

<400> SEQUENCE: 1
cccgtccccg gcgcggcccg cgcgctcctc cgccgcctct cgcctgcgcc atggccggcc      60
ggtcccaccc gggcccgctg cggccgctgc tgccgctcct tgtggtggcc gcgtgcgtcc     120
tgcccggagc cggcgggaca tgcccggagc gcgcgctgga gcggcgcgag gaggaggcga     180
acgtggtgct caccgggacg gtggaggaga tcctcaacgt ggacccggtg cagcacacgt     240
actcctgcaa ggttcgggtc tggcggtact tgaagggcaa agacctggtg gcccgggaga     300
gcctgctgga cggcggcaac aaggtggtga tcagcggctt tggagacccc ctcatctgtg     360
acaaccaggt gtccactggg gacaccagga tcttctttgt gaaccctgca cccccatacc     420
tgtggccagc ccacaagaac gagctgatgc tcaactccag cctcatgcgg atcaccctgc     480
ggaacctgga ggaggtggag ttctgtgtgg aagataaacc cgggacccac ttcactccag     540
tgcctccgac gcctcctgat gcgtgccggg gaatgctgtg cggcttcggc gccgtgtgcg     600
agcccaacgc ggaggggccg ggccgggcgt cctgcgtctg caagaagagc ccgtgcccca     660
gcgtggtggc gcctgtgtgt gggtcggacg cctccaccta cagcaacgaa tgcgagctgc     720
agcgggcgca gtgcagccag cagcgccgca tccgcctgct cagccgcggg ccgtgcggct     780
cgcgggaccc ctgctccaac gtgacctgca gcttcggcag cacctgtgcg cgctcggcca     840
acgggctgac ggcctcgtgc ctgtgccccg cgacctgccg tggcgccccc gaggggaccg     900
tctgcggcag cgacggcgcc gactacccog gcgagtgcca gctcctgcgc cgcgcctgcg     960
cccgccagga gaatgtcttc aagaagttcg acggcccttg tgaccctgt cagggcgccc    1020 tccctgaccc gagccgcagc tgccgtgtga acccgcgcac gcggcgccct gagatgctcc    1080
tacggcccga gagctgccct gcccggcagg cgccagtgtg tggggacgac ggagtcacct    1140
acgaaaacga ctgtgtcatg ggccgatcgg gggccgcccg gggtctcctc ctgcagaaag    1200
tgcgctccgg ccagtgccag ggtcgagacc agtgcccgga gccctgccgg ttcaatgccg    1260
tgtgcctgtc ccgccgtggc cgtccccgct gctcctgcga ccgcgtcacc tgtgacgggg    1320
cctacaggcc cgtgtgtgcc caggacgggc gcacgtatga cagtgattgc tggcggcagc    1380
aggctgagtg ccggcagcag cgtgccatcc ccagcaagca ccagggcccg tgtgaccagg    1440
ccccgtcccc atgcctcggg gtgcagtgtg catttgggc gacgtgtgct gtgaagaacg    1500
ggcaggcagc gtgtgaatgc ctgcaggcgt gctcgagcct ctacgatcct gtgtgcggca    1560
```

-continued

```
gcgacggcgt cacatacggc agcgcgtgcg agctggaggc cacggcctgt accctcgggc    1620
gggagatcca ggtggcgcgc aaaggaccct gtgaccgctg cgggcagtgc cgctttggag    1680
ccctgtgcga ggccgagacc gggcgctgcg tgtgcccctc tgaatgcgtg gctttggccc    1740
agcccgtgtg tggctccgac gggcacacgt accccagcga gtgcatgctg cacgtgcacg    1800
cctgcacaca ccagatcagc ctgcacgtgg cctcagctgg accctgtgag acctgtggag    1860
atgccgtgtg tgcttttggg gctgtgtgct ccgcagggca gtgtgtgtgt ccccggtgtg    1920 agcaccccc gcccggcccc gtgtgtggca gcgacggtgt cacctacggc agtgcctgcg    1980
agctacggga agccgcctgc ctccagcaga cacagatcga ggaggccgg gcagggccgt    2040 gcgagcaggc cgagtgcggt tccggaggct ctggctctgg ggaggacggt gactgtgagc    2100
aggagctgtg ccggcagcgc ggtggcatct gggacgagga ctcggaggac gggccgtgtg    2160
tctgtgactt cagctgccag agtgtcccag gcagcccggt gtgcggctca gatggggtca    2220
cctacagcac cgagtgtgag ctgaagaagg ccaggtgtga gtcacagcga gggctctacg    2280
tagcggccca gggagcctgc cgaggcccca ccttcgcccc gctgccgcct gtggcccct    2340 tacactgtgc ccagacgccc tacggctgct gccaggacaa tatcaccgca gcccggggcg    2400
tgggcctggc tggctgcccc agtgcctgcc agtgcaaccc ccatggctct tacgcggca    2460 cctgtgaccc agccacaggc cagtgctcct gccgcccagg tgtgggggc ctcaggtgtg    2520 accgctgtga gcctggcttc tggaactttc gaggcatcgt caccgatggc cggagtggct    2580
gtacaccctg cagctgtgat ccccaaggcg ccgtgcggga tgactgtgag cagatgacgg    2640
ggctgtgctc gtgtaagccc ggggtggctg acccaagtg tgggcagtgt ccagacggcc    2700
gtgccctggg ccccgcgggc tgtgaagctg acgcttctgc gcctgcgacc tgtgcggaga    2760
tgcgctgtga gttcggtgcg cggtgcgtgg aggagtctgg ctcagcccac tgtgtctgcc    2820
cgatgctcac ctgtccagag gccaacgcta ccaaggtctg tgggtcagat ggagtcacat    2880
acggcaacga gtgtcagctg aagaccatcg cctgccgcca gggcctgcaa atctctatcc    2940
agagcctggg cccgtgccag gaggctgttg ctcccagcac tcacccgaca tctgcctccg    3000
tgactgtgac caccccaggg ctcctcctga gccaggcact gccggccccc ccggcgccc    3060 tcccctgc tcccagcagt accgcacaca gccagaccac ccctccgccc tcatcacgac    3120
ctcggaccac tgccagcgtc ccaggacca ccgtgtggcc cgtgctgacg gtgccccca    3180 cggcaccctc ccctgcaccc agcctggtgg cgtccgcctt tggtgaatct ggcagcactg    3240
atggaagcag cgatgaggaa ctgagcgggg accaggaggc cagtggggt ggctctgggg    3300 ggctcgagcc cttggagggc agcagcgtgg ccaccctgg gccacctgtc gagagggctt    3360
cctgctacaa ctccgcgttg ggctgctgct ctgatgggaa gacgccctcg ctggacgcag    3420
agggctccaa ctgccccgcc accaaggtgt tccagggcgt cctggagctg gagggcgtcg    3480
agggccagga gctgttctac acgcccgaga tggctgaccc caagtcagaa ctgttcgggg    3540
agacagccag gagcattgag agcaccctgg acgacctctt ccggaattca gacgtcaaga    3600
aggattttcg gagtgtccgc ttgcgggacc tggggcccgg caaatccgtc cgcgccattg    3660
tggatgtgca ctttgacccc accacagcct tcagggcacc cgacgtggcc cgggccctgc    3720
tccggcagat ccaggtgtcc aggcgccggt ccttggggt gaggcggccg ctgcaggagc    3780
acgtgcgatt tatggactt gactggtttc ctgcgtttat cacgggggcc acgtcaggag    3840
ccattgctgc gggagccacg gccagagcca ccactgcatc gcgcctgccg tcctctgctg    3900 tgaccctcg ggccccgcac cccagtcaca caagccagcc cgttgccaag accacggcag    3960
```

```
cccccaccac acgtcggccc cccaccactg cccccagccg tgtgcccgga cgtcggcccc    4020
cggcccccca gcagcctcca aagccctgtg actcacagcc ctgcttccac ggggggacct    4080
gccaggactg ggcattgggc gggggcttca cctgcagctg cccggcaggc agggagggcg    4140
ccgtctgtga gaaggtgctt ggcgcccctg tgccggcctt cgagggccgc tccttcctgg    4200
ccttccccac tctccgcgcc taccacacgc tgcgcctggc actggaattc cgggcgctgg    4260
agcctcaggg gctgctgctg tacaatggca acgcccgggg caaggacttc ctggcattgg    4320
cgctgctaga tggccgcgtg cagctcaggt ttgacacagg ttcggggccg gcggtgctga    4380
ccagtgccgt gccggtagag ccgggccagt ggcaccgcct ggagctgtcc cggcactggc    4440
gccggggcac cctctcggtg gatggtgaga cccctgttct gggcgagagt cccagtggca    4500
ccgacggcct caacctggac acagacctct tgtgggcgg cgtacccgag gaccaggctg    4560
ccgtggcgct ggagcggacc ttcgtgggcg ccggcctgag ggggtgcatc cgtttgctgg    4620
acgtcaacaa ccagcgcctg gagcttggca ttgggccggg ggctgccacc cgaggctctg    4680
gcgtgggcga gtgcggggac cacccctgcc tgcccaaccc ctgccatggc ggggcccat    4740 gccagaacct ggaggctgga aggttccatt gccagtgccc gccggccgc gtcggaccaa    4800 cctgtgccga tgagaagagc ccctgccagc ccaacccctg ccatggggcg gcgccctgcc    4860
gtgtgctgcc cgagggtggt gctcagtgcg agtgccccct ggggcgtgag ggcaccttct    4920
gccagacagc ctcggggcag gacggctctg ggcccttcct ggctgacttc aacggcttct    4980
cccacctgga gctgagaggc ctgcacacct ttgcacggga cctgggggag aagatggcgc    5040
tggaggtcgt gttcctggca cgaggcccca gcggcctcct gctctacaac gggcagaaga    5100 cggacgcaa gggggacttc gtgtcgctgg cactgcggga ccgccgcctg gagttccgct    5160
acgacctggg caagggggca gcggtcatca ggagcaggga gccagtcacc ctgggagcct    5220
ggaccagggt ctcactggag cgaaacggcc gcaagggtgc cctgcgtgtg ggcgacggcc    5280
cccgtgtgtt gggggagtcc ccggttccgc acaccgtcct caacctgaag gagccgctct    5340
acgtaggggg cgctcccgac ttcagcaagc tgcccgtgc tgctgccgtg tcctctggct    5400
tcgacggtgc catccagctg gtctccctcg gaggccgcca gctgctgacc ccggagcacg    5460
tgctgcggca ggtggacgtc acgtcctttg caggtcaccc ctgcacccgg gcctcaggcc    5520
acccctgcct caatggggcc tcctgcgtcc gagggaggc tgcctatgtg tgcctgtgtc    5580 ccggggatt ctcaggaccg cactgcgaga agggctggt ggagaagtca gcggggggcg    5640
tggatacctt ggcctttgac gggcggacct ttgtcgagta cctcaacgct gtgaccgaga    5700
gcgagaaggc actgcagagc aaccactttg aactgagcct gcgcactgag gccacgcagg    5760
ggctggtgct ctggagtggc aaggccacgg agcgggcaga ctatgtggca ctggccattg    5820
tggacgggca cctgcaactg agctacaacc tgggctccca gcccgtggtg ctgcgttcca    5880
ccgtgcccgt caacaccaac cgctggttgc gggtcgtggc acatagggag cagagggaag    5940
gttccctgca ggtgggcaat gaggcccctg tgaccggctc ctccccgctg gcgccacgc    6000 agctggacac tgatggagcc ctgtggcttg ggggcctgcc ggagctgccc gtgggcag    6060 cactgcccaa ggcctacggc acaggctttg tgggctgctt gcgggacgtg gtggtgggcc    6120
ggcacccgct gcacctgctg gaggacgccg tcaccaagcc agagctgcgg ccctgcccca    6180
ccccatgagc tggcaccaga gccccgcgcc cgctgtaatt atttctatt tttgtaaact    6240 tgttgctttt tgatatgatt tcttgcctg agtgttggcc ggagggactg ctggccggc    6300
```

```
ctcccttccg tccaggcagc cgtgctgcag acagacctag tgccgaggga tggacaggcg    6360
aggtggcagc gtggagggct cggcgtggat ggcagcctca ggacacacac ccctgcctca    6420
aggtgctgag cccccgcctt gcactgcgcc tgccccacgg tgtccccgcc gggaagcagc    6480
cccggctcct gaatcaccct cgctccgtca ggcgggactc gtgtcccaga gaggaagggg    6540
ctgctgaggt ctgatggggc ccttcctccg ggtgacccca cagggccttt ccaagccccc    6600
atttgagctg ctccttcctg tgtgtgctct gggccctgcc tcggcctcct gcgccaatac    6660
tgtgacttcc aaacaatgtt actgctgggc acagctctgc gttgctcccg tgctgcctgc    6720
gccagcccca ggctgctgag gagcagaggc cagaccaggg ccgatctggg tgtcctgacc    6780
ctcagctggc cctgcccagc caccctggac gtgaccgtat ccctctgcca caccccaggc    6840
cctgcgaggg gctatcgaga ggagctcact gtgggatggg gttgacctct gccgcctgcc    6900
tgggtatctg ggcctggcca tggctgtgtt cttcatgtgt tgattttatt tgaccccctgg   6960
agtggtgggt ctcatctttc ccatctcgcc tgagagcggc tgagggctgc ctcactgcaa    7020
atcctcccca cagcgtcagt gaaagtcgtc cttgtctcag aatgaccagg ggccagccag    7080
tgtctgacca aggtcaaggg gcaggtgcag aggtggcagg gatggctccg aagccagaaa    7140
tgccttaaac tgcaacgtcc cgtcccttcc ccaccccat cccatcccca cccccagccc     7200
cagcccagtc ctcctaggag caggacccga tgaagcgggc ggcggtgggg ctgggtgccg    7260
tgttactaac tctagtatgt ttctgtgtca atcgctgtga ataaagtct gaaaacttta     7320
aaagcaaaaa aaaaaaaaaa aaa                                            7343
```

<210> SEQ ID NO 2
<211> LENGTH: 2045
<212> TYPE: PRT
<213> ORGANISM: Homo sapiens

<400> SEQUENCE: 2

```
Met Ala Gly Arg Ser His Pro Gly Pro Leu Arg Pro Leu Leu Pro Leu
  1               5                  10                  15

Leu Val Ala Ala Cys Val Leu Pro Gly Ala Gly Gly Thr Cys Pro
             20                  25                  30

Glu Arg Ala Leu Glu Arg Arg Glu Glu Ala Asn Val Val Leu Thr
         35                  40                  45

Gly Thr Val Glu Glu Ile Leu Asn Val Asp Pro Val Gln His Thr Tyr
     50                  55                  60

Ser Cys Lys Val Arg Val Trp Arg Tyr Leu Lys Gly Lys Asp Leu Val
 65                  70                  75                  80

Ala Arg Glu Ser Leu Leu Asp Gly Gly Asn Lys Val Val Ile Ser Gly
                 85                  90                  95

Phe Gly Asp Pro Leu Ile Cys Asp Asn Gln Val Ser Thr Gly Asp Thr
            100                 105                 110

Arg Ile Phe Phe Val Asn Pro Ala Pro Pro Tyr Leu Trp Pro Ala His
        115                 120                 125

Lys Asn Glu Leu Met Leu Asn Ser Ser Leu Met Arg Ile Thr Leu Arg
    130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
            180                 185                 190
```

```
Ala Ser Cys Val Cys Lys Lys Ser Pro Cys Pro Ser Val Val Ala Pro
        195                 200                 205

Val Cys Gly Ser Asp Ala Ser Thr Tyr Ser Asn Glu Cys Glu Leu Gln
    210                 215                 220

Arg Ala Gln Cys Ser Gln Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
            260                 265                 270

Pro Ala Thr Cys Arg Gly Ala Pro Glu Gly Thr Val Cys Gly Ser Asp
        275                 280                 285

Gly Ala Asp Tyr Pro Gly Glu Cys Gln Leu Leu Arg Arg Ala Cys Ala
    290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
                325                 330                 335

Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
        355                 360                 365

Val Met Gly Arg Ser Gly Ala Ala Arg Gly Leu Leu Leu Gln Lys Val
    370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
                405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
        435                 440                 445

Gln Gln Arg Ala Ile Pro Ser Lys His Gln Gly Pro Cys Asp Gln Ala
    450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
                485                 490                 495

Leu Tyr Asp Pro Val Cys Gly Ser Asp Gly Val Thr Tyr Gly Ser Ala
            500                 505                 510

Cys Glu Leu Glu Ala Thr Ala Cys Thr Leu Gly Arg Glu Ile Gln Val
        515                 520                 525

Ala Arg Lys Gly Pro Cys Asp Arg Cys Gly Gln Cys Arg Phe Gly Ala
    530                 535                 540

Leu Cys Glu Ala Glu Thr Gly Arg Cys Val Cys Pro Ser Glu Cys Val
545                 550                 555                 560

Ala Leu Ala Gln Pro Val Cys Gly Ser Asp Gly His Thr Tyr Pro Ser
                565                 570                 575

Glu Cys Met Leu His Val His Ala Cys Thr His Gln Ile Ser Leu His
            580                 585                 590

Val Ala Ser Ala Gly Pro Cys Glu Thr Cys Gly Asp Ala Val Cys Ala
        595                 600                 605
```

-continued

```
Phe Gly Ala Val Cys Ser Ala Gly Gln Cys Val Cys Pro Arg Cys Glu
610                 615                 620
His Pro Pro Pro Gly Pro Val Cys Gly Ser Asp Gly Val Thr Tyr Gly
625                 630                 635                 640
Ser Ala Cys Glu Leu Arg Glu Ala Ala Cys Leu Gln Gln Thr Gln Ile
                645                 650                 655
Glu Glu Ala Arg Ala Gly Pro Cys Glu Gln Ala Glu Cys Gly Ser Gly
                660                 665                 670
Gly Ser Gly Ser Gly Glu Asp Gly Asp Cys Glu Gln Glu Leu Cys Arg
                675                 680                 685
Gln Arg Gly Gly Ile Trp Asp Glu Asp Ser Glu Asp Gly Pro Cys Val
690                 695                 700
Cys Asp Phe Ser Cys Gln Ser Val Pro Gly Ser Pro Val Cys Gly Ser
705                 710                 715                 720
Asp Gly Val Thr Tyr Ser Thr Glu Cys Glu Leu Lys Lys Ala Arg Cys
                725                 730                 735
Glu Ser Gln Arg Gly Leu Tyr Val Ala Ala Gln Gly Ala Cys Arg Gly
                740                 745                 750
Pro Thr Phe Ala Pro Leu Pro Pro Val Ala Pro Leu His Cys Ala Gln
                755                 760                 765
Thr Pro Tyr Gly Cys Cys Gln Asp Asn Ile Thr Ala Ala Arg Gly Val
770                 775                 780
Gly Leu Ala Gly Cys Pro Ser Ala Cys Gln Cys Asn Pro His Gly Ser
785                 790                 795                 800
Tyr Gly Gly Thr Cys Asp Pro Ala Thr Gly Gln Cys Ser Cys Arg Pro
                805                 810                 815
Gly Val Gly Gly Leu Arg Cys Asp Arg Cys Glu Pro Gly Phe Trp Asn
                820                 825                 830
Phe Arg Gly Ile Val Thr Asp Gly Arg Ser Gly Cys Thr Pro Cys Ser
                835                 840                 845
Cys Asp Pro Gln Gly Ala Val Arg Asp Asp Cys Glu Gln Met Thr Gly
850                 855                 860
Leu Cys Ser Cys Lys Pro Gly Val Ala Gly Pro Lys Cys Gly Gln Cys
865                 870                 875                 880
Pro Asp Gly Arg Ala Leu Gly Pro Ala Gly Cys Glu Ala Asp Ala Ser
                885                 890                 895
Ala Pro Ala Thr Cys Ala Glu Met Arg Cys Glu Phe Gly Ala Arg Cys
                900                 905                 910
Val Glu Glu Ser Gly Ser Ala His Cys Val Cys Pro Met Leu Thr Cys
                915                 920                 925
Pro Glu Ala Asn Ala Thr Lys Val Cys Gly Ser Asp Gly Val Thr Tyr
930                 935                 940
Gly Asn Glu Cys Gln Leu Lys Thr Ile Ala Cys Arg Gln Gly Leu Gln
945                 950                 955                 960
Ile Ser Ile Gln Ser Leu Gly Pro Cys Gln Glu Ala Val Ala Pro Ser
                965                 970                 975
Thr His Pro Thr Ser Ala Ser Val Thr Val Thr Thr Pro Gly Leu Leu
                980                 985                 990
Leu Ser Gln Ala Leu Pro Ala Pro Pro Gly Ala Leu Pro Leu Ala Pro
                995                 1000                1005
Ser Ser Thr Ala His Ser Gln Thr Pro Pro Pro Ser Ser Arg Pro
                1010                1015                1020
Arg Thr Thr Ala Ser Val Pro Arg Thr Thr Val Trp Pro Val Leu Thr
```

```
                1025                1030                1035                1040
Val Pro Pro Thr Ala Pro Ser Pro Ala Pro Ser Leu Val Ala Ser Ala
            1045                1050                1055

Phe Gly Glu Ser Gly Ser Thr Asp Gly Ser Ser Asp Glu Glu Leu Ser
            1060                1065                1070

Gly Asp Gln Glu Ala Ser Gly Gly Ser Gly Gly Leu Glu Pro Leu
        1075                1080                1085

Glu Gly Ser Ser Val Ala Thr Pro Gly Pro Val Glu Arg Ala Ser
    1090                1095                1100

Cys Tyr Asn Ser Ala Leu Gly Cys Cys Ser Asp Gly Lys Thr Pro Ser
1105                1110                1115                1120

Leu Asp Ala Glu Gly Ser Asn Cys Pro Ala Thr Lys Val Phe Gln Gly
            1125                1130                1135

Val Leu Glu Leu Glu Gly Val Glu Gly Gln Leu Phe Tyr Thr Pro
        1140                1145                1150

Glu Met Ala Asp Pro Lys Ser Glu Leu Phe Gly Glu Thr Ala Arg Ser
        1155                1160                1165

Ile Glu Ser Thr Leu Asp Asp Leu Phe Arg Asn Ser Asp Val Lys Lys
    1170                1175                1180

Asp Phe Arg Ser Val Arg Leu Arg Asp Leu Gly Pro Gly Lys Ser Val
1185                1190                1195                1200

Arg Ala Ile Val Asp Val His Phe Asp Pro Thr Thr Ala Phe Arg Ala
            1205                1210                1215

Pro Asp Val Ala Arg Ala Leu Leu Arg Gln Ile Gln Val Ser Arg Arg
        1220                1225                1230

Arg Ser Leu Gly Val Arg Arg Pro Leu Gln Glu His Val Arg Phe Met
        1235                1240                1245

Asp Phe Asp Trp Phe Pro Ala Phe Ile Thr Gly Ala Thr Ser Gly Ala
        1250                1255                1260

Ile Ala Ala Gly Ala Thr Ala Arg Ala Thr Thr Ala Ser Arg Leu Pro
1265                1270                1275                1280

Ser Ser Ala Val Thr Pro Arg Ala Pro His Pro Ser His Thr Ser Gln
            1285                1290                1295

Pro Val Ala Lys Thr Thr Ala Ala Pro Thr Thr Arg Arg Pro Pro Thr
        1300                1305                1310

Thr Ala Pro Ser Arg Val Pro Gly Arg Arg Pro Pro Ala Pro Gln Gln
        1315                1320                1325

Pro Pro Lys Pro Cys Asp Ser Gln Pro Cys Phe His Gly Gly Thr Cys
    1330                1335                1340

Gln Asp Trp Ala Leu Gly Gly Gly Phe Thr Cys Ser Cys Pro Ala Gly
1345                1350                1355                1360

Arg Gly Gly Ala Val Cys Glu Lys Val Leu Gly Ala Pro Val Pro Ala
            1365                1370                1375

Phe Glu Gly Arg Ser Phe Leu Ala Phe Pro Thr Leu Arg Ala Tyr His
        1380                1385                1390

Thr Leu Arg Leu Ala Leu Glu Phe Arg Ala Leu Glu Pro Gln Gly Leu
        1395                1400                1405

Leu Leu Tyr Asn Gly Asn Ala Arg Gly Lys Asp Phe Leu Ala Leu Ala
        1410                1415                1420

Leu Leu Asp Gly Arg Val Gln Leu Arg Phe Asp Thr Gly Ser Gly Pro
1425                1430                1435                1440

Ala Val Leu Thr Ser Ala Val Pro Val Glu Pro Gly Gln Trp His Arg
            1445                1450                1455
```

```
Leu Glu Leu Ser Arg His Trp Arg Arg Gly Thr Leu Ser Val Asp Gly
        1460                1465                1470
Glu Thr Pro Val Leu Gly Glu Ser Pro Ser Gly Thr Asp Gly Leu Asn
    1475                1480                1485
Leu Asp Thr Asp Leu Phe Val Gly Gly Val Pro Glu Asp Gln Ala Ala
    1490                1495                1500
Val Ala Leu Glu Arg Thr Phe Val Gly Ala Gly Leu Arg Gly Cys Ile
1505                1510                1515                1520
Arg Leu Leu Asp Val Asn Asn Gln Arg Leu Glu Leu Gly Ile Gly Pro
        1525                1530                1535
Gly Ala Ala Thr Arg Gly Ser Gly Val Gly Glu Cys Gly Asp His Pro
        1540                1545                1550
Cys Leu Pro Asn Pro Cys His Gly Gly Ala Pro Cys Gln Asn Leu Glu
        1555                1560                1565
Ala Gly Arg Phe His Cys Gln Cys Pro Pro Gly Arg Val Gly Pro Thr
    1570                1575                1580
Cys Ala Asp Glu Lys Ser Pro Cys Gln Pro Asn Pro Cys His Gly Ala
1585                1590                1595                1600
Ala Pro Cys Arg Val Leu Pro Glu Gly Gly Ala Gln Cys Glu Cys Pro
        1605                1610                1615
Leu Gly Arg Glu Gly Thr Phe Cys Gln Thr Ala Ser Gly Gln Asp Gly
        1620                1625                1630
Ser Gly Pro Phe Leu Ala Asp Phe Asn Gly Phe Ser His Leu Glu Leu
        1635                1640                1645
Arg Gly Leu His Thr Phe Ala Arg Asp Leu Gly Glu Lys Met Ala Leu
        1650                1655                1660
Glu Val Val Phe Leu Ala Arg Gly Pro Ser Gly Leu Leu Leu Tyr Asn
1665                1670                1675                1680
Gly Gln Lys Thr Asp Gly Lys Gly Asp Phe Val Ser Leu Ala Leu Arg
        1685                1690                1695
Asp Arg Arg Leu Glu Phe Arg Tyr Asp Leu Gly Lys Gly Ala Ala Val
        1700                1705                1710
Ile Arg Ser Arg Glu Pro Val Thr Leu Gly Ala Trp Thr Arg Val Ser
        1715                1720                1725
Leu Glu Arg Asn Gly Arg Lys Gly Ala Leu Arg Val Gly Asp Gly Pro
        1730                1735                1740
Arg Val Leu Gly Glu Ser Pro Val Pro His Thr Val Leu Asn Leu Lys
1745                1750                1755                1760
Glu Pro Leu Tyr Val Gly Gly Ala Pro Asp Phe Ser Lys Leu Ala Arg
        1765                1770                1775
Ala Ala Ala Val Ser Ser Gly Phe Asp Gly Ala Ile Gln Leu Val Ser
        1780                1785                1790
Leu Gly Gly Arg Gln Leu Leu Thr Pro Glu His Val Leu Arg Gln Val
        1795                1800                1805
Asp Val Thr Ser Phe Ala Gly His Pro Cys Thr Arg Ala Ser Gly His
        1810                1815                1820
Pro Cys Leu Asn Gly Ala Ser Cys Val Pro Arg Glu Ala Ala Tyr Val
1825                1830                1835                1840
Cys Leu Cys Pro Gly Gly Phe Ser Gly Pro His Cys Glu Lys Gly Leu
        1845                1850                1855
Val Glu Lys Ser Ala Gly Asp Val Asp Thr Leu Ala Phe Asp Gly Arg
        1860                1865                1870
```

-continued

Thr Phe Val Glu Tyr Leu Asn Ala Val Thr Glu Ser Glu Lys Ala Leu
    1875                1880                1885

Gln Ser Asn His Phe Glu Leu Ser Leu Arg Thr Glu Ala Thr Gln Gly
    1890                1895                1900

Leu Val Leu Trp Ser Gly Lys Ala Thr Glu Arg Ala Asp Tyr Val Ala
1905                1910                1915                1920

Leu Ala Ile Val Asp Gly His Leu Gln Leu Ser Tyr Asn Leu Gly Ser
            1925                1930                1935

Gln Pro Val Val Leu Arg Ser Thr Val Pro Val Asn Thr Asn Arg Trp
        1940                1945                1950

Leu Arg Val Val Ala His Arg Glu Gln Arg Glu Gly Ser Leu Gln Val
    1955                1960                1965

Gly Asn Glu Ala Pro Val Thr Gly Ser Ser Pro Leu Gly Ala Thr Gln
    1970                1975                1980

Leu Asp Thr Asp Gly Ala Leu Trp Leu Gly Gly Leu Pro Glu Leu Pro
1985                1990                1995                2000

Val Gly Pro Ala Leu Pro Lys Ala Tyr Gly Thr Gly Phe Val Gly Cys
            2005                2010                2015

Leu Arg Asp Val Val Val Gly Arg His Pro Leu His Leu Leu Glu Asp
        2020                2025                2030

Ala Val Thr Lys Pro Glu Leu Arg Pro Cys Pro Thr Pro
            2035                2040                2045

<210> SEQ ID NO 3
<211> LENGTH: 8244
<212> TYPE: DNA
<213> ORGANISM: Homo sapiens

<400> SEQUENCE: 3
gtggccgggg ctgcggcgcg ggggcgggg cggtcgggcc cgggacaccc cctcccggtc      60
ccctggcggg gcagcgtcgg ctctggcagc actggaggcg gcggcggccc gagggcgact     120
tgcggggcgc gcaggccgcc gtgcacccgg gacgcttccc cctcggggac cctccgcggg     180
cttctccgcc gcgccgtccg gcgggagccg gcgggacccc gggcgagcgg cgcgggcggc     240
accatgaggc ggcagtgggg cgcgctgctg cttggcgccc tgctctgcgc acacggcctg     300
gccagcagcc ccgagtgtgc ttgtggtcgg agccacttca catgtgcagt gagtgctctt     360
ggagagtgta cctgcatccc tgcccagtgg cagtgtgatg agacaatga ctgcggggac      420 cacagcgatg aggatggatg tatactacct acctgttccc ctcttgactt tcactgtgac     480
aatggcaagt gcatccgccg ctcctgggtg tgtgacgggg acaacgactg tgaggatgac     540
tcggatgagc aggactgtcc cccccgggag tgtgaggagg acgagtttcc ctgccagaat     600
ggctactgca tccggagtct gtggcactgc gatggtgaca atgactgtgg cgacaacagc     660
gatgagcagt gtgacatgcg caagtgctcc gacaaggagt tccgctgtag tgacggaagc     720
tgcattgctg agcattggta ctgcgacggt gacaccgact gcaaagatgg ctccgatgag     780
gagaactgtc cctcagcagt gccagcgccc cctgcaacc tggaggagtt ccagtgtgcc     840
tatggacgct gcatcctcga catctaccac tgcgatggcg acgatgactg tggagactgg     900
tcagacgagt ctgactgctc ctcccaccag ccctgccgct tggggagtt catgtgtgac     960 agtggcctgt gcatcaatgc aggctggcgc tgcgatggtg acgcggactg tgatgaccag    1020
tctgatgagc gcaactgcac cacctccatg tgtacggcag aacagttccg ctgtcactca    1080
ggccgctgtg tccgcctgtc ctggcgctgt gatggggagg acgactgtgc agacaacagc    1140

```
gatgaagaga actgtgagaa tacaggaagc ccccaatgtg ccttggacca gttcctgtgt   1200
tggaatgggc gctgcattgg gcagaggaag ctgtgcaacg gggtcaacga ctgtggtgac   1260
aacagcgacg aaagcccaca gcagaattgc cggccccgga cgggtgagga gaactgcaat   1320
gttaacaacg gtggctgtgc ccagaagtgc cagatggtgc gggggggcagt gcagtgtacc   1380 tgccacacag gctaccggct cacagaggat gggcacacgt gccaagatgt gaatgaatgt   1440
gccgaggagg ggtattgcag ccagggctgc accaacagcg aagggctttt ccaatgctgg   1500
tgtgaaacag gctatgaact acggcccgac cggcgcagct gcaaggctct ggggccagag   1560
cctgtgctgc tgttcgccaa tcgcatcgac atccggcagg tgctgccaca ccgctctgag   1620
tacacactgc tgcttaacaa cctggagaat gccattgccc ttgatttcca ccaccgccgc   1680
gagcttgtct tctggtcaga tgtcaccctg gaccggatcc tccgtgccaa cctcaacggc   1740
agcaacgtgg aggaggttgt gtctactggg ctggagagcc caggggcct ggctgtggat    1800 tgggtccatg acaaactcta ctggaccgac tcaggcacct cgaggattga ggtggccaat   1860
ctggatgggg cccaccggaa agtgttgctg tggcagaacc tggagaagcc ccgggccatt   1920
gccttgcatc ccatggaggg taccatttac tggacagact ggggcaacac ccccgtatt    1980 gaggcctcca gcatggatgg ctctggacgc cgcatcattg ccgatacccca tctcttctgg   2040 cccaatggcc tcaccatcga ctatgccggg cgccgtatgt actgggtgga tgctaagcac   2100
catgtcatcg agagggccaa tctggatggg agtcaccgta aggctgtcat tagccagggc   2160
ctcccgcatc ccttcgccat cacagtgttt gaagacagcc tgtactggac agactggcac   2220
accaagagca tcaatagcgc taacaaattt acggggaaga accaggaaat cattcgcaac   2280
aaactccact ccctatggga catccacacc ttgcaccccc agcgccaacc tgcagggaaa   2340
aaccgctgtg gggacaacaa cggaggctgc acgcacctgt gtctgcccag tggcagaac    2400 tacacctgtg cctgccccac tggcttccgc aagatcagca gccacgcctg tgcccagagt   2460
cttgacaagt tcctgctttt tgcccgaagg atggacatcc gtcgaatcag ctttgacaca   2520
gaggacctgt ctgatgatgt catcccactg gctgacgtgc gcagtgctgt ggcccttgac   2580
tgggactccc gggatgacca cgtgtactgg acagatgtca gcactgatac catcagcagg   2640
gccaagtggg atggaacagg acaggaggtg gtagtggata ccagtttgga gagcccagct   2700
ggcctggcca ttgattgggt caccaacaaa ctgtactgga cagatgcagg tacagaccgg   2760
attgaagtag ccaacacaga tggcagcatg agaacagtac tcatctggga gaaccttgat   2820
cgtcctcggg acatcgtggt ggaacccatg ggcgggtaca tgtattggac tgactggggt   2880
gcgagcccca agattgaacg agctggcatg gatgcctcag gccgccaagt cattatctct   2940
tctaatctga cctggcctaa tgggttagct attgattatg ggtcccagcg tctatactgg   3000
gctgacgccg gcatgaagac aattgaattt gctggactgg atggcagtaa gaggaaggtg   3060
ctgattggaa gccagctccc ccacccattt gggctgaccc tctatggaga gcgcatctat   3120
tggactgact ggcagaccaa gagcatacag agcgctgacc ggctgacagg gctggaccgg   3180
gagactctgc aggagaacct ggaaaaccta atggacatcc atgtcttcca ccgccgccgg   3240
cccccagtgt ctacaccatg tgctatggag aatggcggct gtagccacct gtgtcttagg   3300
tccccaaatc caagcggatt cagctgtacc tgccccacag gcatcaacct gctgtctgat   3360
ggcaagacct gctcaccagg catgaacagt ttcctcatct tcgccaggag gatagacatt   3420
cgcatggtct ccctggacat cccttatttt gctgatgtgg tggtaccaat caacattacc   3480
atgaagaaca ccattgccat tggagtagac ccccaggaag gaaaggtgta ctggtctgac   3540
```

```
agcacactgc acaggatcag tcgtgccaat ctggatggct cacagcatga ggacatcatc   3600
accacagggc tacagaccac agatgggctc gcggttgatg ccattggccg gaaagtatac   3660
tggacagaca cgggaacaaa ccggattgaa gtgggcaacc tggacgggtc catgcggaaa   3720
gtgttggtgt ggcagaacct tgacagtccc cgggccatcg tactgtacca tgagatgggg   3780
tttatgtact ggacagactg gggggagaat gccaagttag agcggtccgg aatggatggc   3840
tcagaccgcg cggtgctcat caacaacaac ctaggatggc ccaatggact gactgtggac   3900
aaggccagct cccaactgct atgggccgat gcccacaccg agcgaattga ggctgctgac   3960
ctgaatggtg ccaatcggca tacattggtg tcaccggtgc agcacccata tggcctcacc   4020
ctgctcgact cctatatcta ctggactgac tggcagactc ggagcatcca ccgtgctgac   4080
aagggtactg gcagcaatgt catcctcgtg aggtccaacc tgccaggcct catggacatg   4140
caggctgtgg accgggcaca gccactaggt tttaacaagt gcggctcgag aaatggcggc   4200
tgctcccacc tctgcttgcc tcggccttct ggcttctcct gtgcctgccc cactggcatc   4260
cagctgaagg gagatgggaa gacctgtgat ccctctcctg agacctacct gctcttctcc   4320
agccgtggct ccatccggcg tatctcactg gacaccagtg accacaccga tgtgcatgtc   4380
cctgttcctg agctcaacaa tgtcatctcc ctggactatg acagcgtgga tggaaaggtc   4440
tattacacag atgtgttcct ggatgttatc aggcgagcag acctgaacgg cagcaacatg   4500
gagacagtga tcgggcgagg gctgaagacc actgacgggc tggcagtgga ctgggtggcc   4560
aggaacctgt actggacaga cacaggtcga ataccattg aggcgtccag gctggatggt   4620
tcctgccgca aagtactgat caacaatagc ctggatgagc cccgggccat tgctgttttc   4680
cccaggaagg ggtacctctt ctggacagac tggggccaca ttgccaagat cgaacgggca   4740
aacttggatg gttctgagcg gaaggtcctc atcaacacag acctgggttg gcccaatggc   4800
cttaccctgg actatgatac ccgcaggatc tactgggtgg atgcgcatct ggaccggatc   4860
gagagtgctg acctcaatgg gaaactgcgg caggtcttgg tcagccatgt gtcccacccc   4920
tttgccctca cacagcaaga caggtggatc tactggacag actggcagac caagtcaatc   4980
cagcgtgttg acaaatactc aggccggaac aaggagacag tgctggcaaa tgtggaagga   5040
ctcatggata tcatcgtggt ttcccctcag cggcagacag ggaccaatgc ctgtggtgtg   5100
aacaatggtg gctgcaccca cctctgcttt gccagagcct cggacttcgt atgtgcctgt   5160
cctgacgaac ctgatagccg gccctgctcc cttgtgcctg gcctggtacc accagctcct   5220
agggctactg gcatgagtga aaagagccca gtgctaccca cacaccacc taccaccttg   5280 tattcttcaa ccacccggac ccgcacgtct ctggaggagg tggaaggaag atgctctgaa   5340
agggatgcca ggctgggcct ctgtgcacgt tccaatgacg ctgttcctgc tgctccaggg   5400
gaaggacttc atatcagcta cgccattggt ggactcctca gtattctgct gattttggtg   5460
gtgattgcag ctttgatgct gtacagacac aaaaaaatcca agttcactga tcctggaatg   5520
gggaacctca cctacagcaa cccctcctac cgaacatcca cacaggaagt gaagattgaa   5580
gcaatcccca aaccagccat gtacaaccag ctgtgctata agaaagaggg agggcctgac   5640
cataactaca ccaaggagaa gatcaagatc gtagaggaa tctgcctcct gtctggggat   5700
gatgctgagt gggatgacct caagcaactg cgaagctcac gggggggcct cctccgggat   5760
catgtatgca tgaagacaga cacgtgtccc atccaggcca gctctggctc cctggatgac   5820
acagagacgg agcagctgtt acaggaagag cagtctgagt gtagcagcgt ccatactgca   5880
```

```
gccactccag aaagacgagg ctctctgcca gacacgggct ggaaacatga acgcaagctc    5940
tcctcagaga gccaggtcta aatgcccaca ttctcttccc tgcctgcctg ttccttctcc    6000
tttatggacg tctagtcctt gtgctcgctt acaccgcagg ccccgcttct gtgtgcttgt    6060
cctcctcctc ctcccacccc ataactgttc ctaagccttc accggagctg tttaccacgt    6120
gagtccataa ctacctgtgc acaagaaatg atggcacatc acgagaattt agacctggat    6180
tttaccatga acctcacatc ttgtactcca tcctgggccc cctgaaactg cttattcgtg    6240
attcctcacc agcgtagagc tccacctccc ctttccccag taccctcagt gcctgcttct    6300
cagtgctgat gcagctgatg acccaggact gcgctctgcc ccatcacagc cagcatgact    6360
gcttctctga gagaacttgc ccatcagggg ctgggacatg ggggtgtggg taaagacagg    6420
gatgaaggat agaggctgag agaagaagga agaatcagcc cagcaggtat gggcatctgg    6480
gaaacctcca gcctcaagtg tgttggtaac atgaaaaagc tttgggggt agttggatct     6540
gggtgtctgg tccattgctg gcagtggaca ttattcttgc cctaagagac actgcctttt    6600
cagcagcaga tactggtgag atgggggtgg ctcaggctgt tcttcctcct cctagaatgt    6660
ctggagctgt ttctacattc agataactgg gtcccctatc acaaggctac tggctaatag    6720
gaattccctc ctggtgccac cactggccag tacctttcct aagtctttgc tcaaattaac    6780
caggttgtga gccagtggct tgagtgaatg ttaggccttg ggggctgagt ctctgaaaag    6840
tctaagaagc tctgcctaga ccaaatatgg tatacctcct gacccctctc tccctcatgt    6900
cctgggattc tggggaagag acctagaaac aagctttcaa agaaaaacca gaagttgtca    6960
taaatggtca gaaagaacga tcaggttgga gacttgggaa acccagggcc taagagaag    7020
tatccatgag ggtcaaactt cctgttgaac ttcctatgtt ctttctcaag tgctcaggga    7080
tctaagttag tggacagcaa gcctgtggct acggggtggt gatgttcctc ttccagctgt    7140
cccctcagct aaggggctta gtttccatgt gggatgccat cacttggttc atgctcattc    7200
acacaaaggg cacgtgtctc agcctggtat cagggaaatt gagacttatt tttgccctaa    7260
aacgtctccc tagctgttct tcgtggggtt ttttttgtttg tttttttgcc taatttgctt    7320
tttctgacca agccttgtgg caccagcaat ctccaaagtc ctgtggtggg agggctgaat    7380
aaataaaaat acaaagaggt gggtaaggag taggaaggta gagagcacca ctgatgaggc    7440
cctcctagcc catggcagac ccagacctct tctcccccag gaattagaag tggcaggaga    7500
gaacaacagg ggctgggaat ggaggggaga atttctaggg gaagtttcct gagttgaaac    7560
ttctcctgtg gttactggta ttgagaaatc agctaccaaa gtgaaaaagg acaagatcaa    7620
ttcttttcta gtcagttcta agactgctag agagagatac caggcccta gccttgctct     7680
cagtagcgtc agccccagtt ctgagcctcc ccacattaca cttaacaagc agtaaaggag    7740
tgagcacttt gggtccttag actcatgtct ggggaggaag agcaagtaga aaagtggcat    7800
tttcttgatt ggaaagggg aaggatctta ttgcacttgg gctgttcaga atgtagaaag     7860
gacatatttg aggaagtatc tatttgagca ctgatttact ctgtaaaaag caaaatctct    7920
ctgtcctaaa ctaatggaag cgattctccc atgctcatgt gtaatggttt taacgttact    7980
cactggagag attggacttt ctggagttat ttaaccacta tgttcagtat ttaggactt     8040
tatgataatt taatataaat ttagcttttc ttaatcacct tgcctggctt ggagtcatga    8100
ctaatcctgc acctgctctg tctggcagac ccatgctgtg gaaacctgc ttacagacat     8160
cacttttaag tcctttgtgg atgtgggcac agtgaagagc aataaagagt gtgaggttcc    8220
tgctggaaaa aaaaaaaaaa aaaa                                           8244
```

<210> SEQ ID NO 4
<211> LENGTH: 1905
<212> TYPE: PRT
<213> ORGANISM: Homo sapiens

<400> SEQUENCE: 4

Met Arg Arg Gln Trp Gly Ala Leu Leu Gly Ala Leu Leu Cys Ala
1               5                   10                  15

His Gly Leu Ala Ser Ser Pro Glu Cys Ala Cys Gly Arg Ser His Phe
                20                  25                  30

Thr Cys Ala Val Ser Ala Leu Gly Glu Cys Thr Cys Ile Pro Ala Gln
                35                  40                  45

Trp Gln Cys Asp Gly Asp Asn Asp Cys Gly Asp His Ser Asp Glu Asp
        50                  55                  60

Gly Cys Ile Leu Pro Thr Cys Ser Pro Leu Asp Phe His Cys Asp Asn
65                  70                  75                  80

Gly Lys Cys Ile Arg Arg Ser Trp Val Cys Asp Gly Asp Asn Asp Cys
                85                  90                  95

Glu Asp Asp Ser Asp Glu Gln Asp Cys Pro Pro Arg Glu Cys Glu Glu
                100                 105                 110

Asp Glu Phe Pro Cys Gln Asn Gly Tyr Cys Ile Arg Ser Leu Trp His
                115                 120                 125

Cys Asp Gly Asp Asn Asp Cys Gly Asp Asn Ser Asp Glu Gln Cys Asp
        130                 135                 140

Met Arg Lys Cys Ser Asp Lys Glu Phe Arg Cys Ser Asp Gly Ser Cys
145                 150                 155                 160

Ile Ala Glu His Trp Tyr Cys Asp Gly Asp Thr Asp Cys Lys Asp Gly
                165                 170                 175

Ser Asp Glu Glu Asn Cys Pro Ser Ala Val Pro Ala Pro Pro Cys Asn
                180                 185                 190

Leu Glu Glu Phe Gln Cys Ala Tyr Gly Arg Cys Ile Leu Asp Ile Tyr
                195                 200                 205

His Cys Asp Gly Asp Asp Cys Gly Asp Trp Ser Asp Glu Ser Asp
        210                 215                 220

Cys Ser Ser His Gln Pro Cys Arg Ser Gly Glu Phe Met Cys Asp Ser
225                 230                 235                 240

Gly Leu Cys Ile Asn Ala Gly Trp Arg Cys Asp Gly Asp Ala Asp Cys
                245                 250                 255

Asp Asp Gln Ser Asp Glu Arg Asn Cys Thr Thr Ser Met Cys Thr Ala
                260                 265                 270

Glu Gln Phe Arg Cys His Ser Gly Arg Cys Val Arg Leu Ser Trp Arg
                275                 280                 285

Cys Asp Gly Glu Asp Asp Cys Ala Asp Asn Ser Asp Glu Glu Asn Cys
        290                 295                 300

Glu Asn Thr Gly Ser Pro Gln Cys Ala Leu Asp Gln Phe Leu Cys Trp
305                 310                 315                 320

Asn Gly Arg Cys Ile Gly Gln Arg Lys Leu Cys Asn Gly Val Asn Asp
                325                 330                 335

Cys Gly Asp Ser Asp Glu Ser Pro Gln Asn Cys Arg Pro Arg
                340                 345                 350

Thr Gly Glu Glu Asn Cys Asn Val Asn Asn Gly Gly Cys Ala Gln Lys
                355                 360                 365

Cys Gln Met Val Arg Gly Ala Val Gln Cys Thr Cys His Thr Gly Tyr

```
                370                 375                 380
Arg Leu Thr Glu Asp Gly His Thr Cys Gln Asp Val Asn Glu Cys Ala
385                 390                 395                 400

Glu Glu Gly Tyr Cys Ser Gln Gly Cys Thr Asn Ser Glu Gly Ala Phe
                405                 410                 415

Gln Cys Trp Cys Glu Thr Gly Tyr Glu Leu Arg Pro Asp Arg Arg Ser
                420                 425                 430

Cys Lys Ala Leu Gly Pro Glu Pro Val Leu Leu Phe Ala Asn Arg Ile
                435                 440                 445

Asp Ile Arg Gln Val Leu Pro His Arg Ser Glu Tyr Thr Leu Leu Leu
                450                 455                 460

Asn Asn Leu Glu Asn Ala Ile Ala Leu Asp Phe His His Arg Arg Glu
465                 470                 475                 480

Leu Val Phe Trp Ser Asp Val Thr Leu Asp Arg Ile Leu Arg Ala Asn
                485                 490                 495

Leu Asn Gly Ser Asn Val Glu Glu Val Val Ser Thr Gly Leu Glu Ser
                500                 505                 510

Pro Gly Gly Leu Ala Val Asp Trp Val His Asp Lys Leu Tyr Trp Thr
                515                 520                 525

Asp Ser Gly Thr Ser Arg Ile Glu Val Ala Asn Leu Asp Gly Ala His
                530                 535                 540

Arg Lys Val Leu Leu Trp Gln Asn Leu Glu Lys Pro Arg Ala Ile Ala
545                 550                 555                 560

Leu His Pro Met Glu Gly Thr Ile Tyr Trp Thr Asp Trp Gly Asn Thr
                565                 570                 575

Pro Arg Ile Glu Ala Ser Ser Met Asp Gly Ser Gly Arg Arg Ile Ile
                580                 585                 590

Ala Asp Thr His Leu Phe Trp Pro Asn Gly Leu Thr Ile Asp Tyr Ala
                595                 600                 605

Gly Arg Arg Met Tyr Trp Val Asp Ala Lys His His Val Ile Glu Arg
                610                 615                 620

Ala Asn Leu Asp Gly Ser His Arg Lys Ala Val Ile Ser Gln Gly Leu
625                 630                 635                 640

Pro His Pro Phe Ala Ile Thr Val Phe Glu Asp Ser Leu Tyr Trp Thr
                645                 650                 655

Asp Trp His Thr Lys Ser Ile Asn Ser Ala Asn Lys Phe Thr Gly Lys
                660                 665                 670

Asn Gln Glu Ile Ile Arg Asn Lys Leu His Phe Pro Met Asp Ile His
                675                 680                 685

Thr Leu His Pro Gln Arg Gln Pro Ala Gly Lys Asn Arg Cys Gly Asp
                690                 695                 700

Asn Asn Gly Gly Cys Thr His Leu Cys Leu Pro Ser Gly Gln Asn Tyr
705                 710                 715                 720

Thr Cys Ala Cys Pro Thr Gly Phe Arg Lys Ile Ser Ser His Ala Cys
                725                 730                 735

Ala Gln Ser Leu Asp Lys Phe Leu Leu Phe Ala Arg Arg Met Asp Ile
                740                 745                 750

Arg Arg Ile Ser Phe Asp Thr Glu Asp Leu Ser Asp Asp Val Ile Pro
                755                 760                 765

Leu Ala Asp Val Arg Ser Ala Val Ala Leu Asp Trp Asp Ser Arg Asp
                770                 775                 780

Asp His Val Tyr Trp Thr Asp Val Ser Thr Asp Thr Ile Ser Arg Ala
785                 790                 795                 800
```

```
Lys Trp Asp Gly Thr Gly Gln Glu Val Val Asp Thr Ser Leu Glu
            805                 810                 815

Ser Pro Ala Gly Leu Ala Ile Asp Trp Val Thr Asn Lys Leu Tyr Trp
            820                 825                 830

Thr Asp Ala Gly Thr Asp Arg Ile Glu Val Ala Asn Thr Asp Gly Ser
            835                 840                 845

Met Arg Thr Val Leu Ile Trp Glu Asn Leu Asp Arg Pro Arg Asp Ile
850                     855                 860

Val Val Glu Pro Met Gly Gly Tyr Met Tyr Trp Thr Asp Trp Gly Ala
865                 870                 875                 880

Ser Pro Lys Ile Glu Arg Ala Gly Met Asp Ala Ser Gly Arg Gln Val
            885                 890                 895

Ile Ile Ser Ser Asn Leu Thr Trp Pro Asn Gly Leu Ala Ile Asp Tyr
            900                 905                 910

Gly Ser Gln Arg Leu Tyr Trp Ala Asp Ala Gly Met Lys Thr Ile Glu
        915                 920                 925

Phe Ala Gly Leu Asp Gly Ser Lys Arg Lys Val Leu Ile Gly Ser Gln
        930                 935                 940

Leu Pro His Pro Phe Gly Leu Thr Leu Tyr Gly Glu Arg Ile Tyr Trp
945                 950                 955                 960

Thr Asp Trp Gln Thr Lys Ser Ile Gln Ser Ala Asp Arg Leu Thr Gly
            965                 970                 975

Leu Asp Arg Glu Thr Leu Gln Glu Asn Leu Glu Asn Leu Met Asp Ile
            980                 985                 990

His Val Phe His Arg Arg Pro Pro Val Ser Thr Pro Cys Ala Met
            995                 1000                1005

Glu Asn Gly Gly Cys Ser His Leu Cys Leu Arg Ser Pro Asn Pro Ser
1010                    1015                1020

Gly Phe Ser Cys Thr Cys Pro Thr Gly Ile Asn Leu Leu Ser Asp Gly
1025                    1030                1035                1040

Lys Thr Cys Ser Pro Gly Met Asn Ser Phe Leu Ile Phe Ala Arg Arg
                1045                1050                1055

Ile Asp Ile Arg Met Val Ser Leu Asp Ile Pro Tyr Phe Ala Asp Val
                1060                1065                1070

Val Val Pro Ile Asn Ile Thr Met Lys Asn Thr Ile Ala Ile Gly Val
            1075                1080                1085

Asp Pro Gln Glu Gly Lys Val Tyr Trp Ser Asp Ser Thr Leu His Arg
    1090                1095                1100

Ile Ser Arg Ala Asn Leu Asp Gly Ser Gln His Glu Asp Ile Ile Thr
1105                1110                1115                1120

Thr Gly Leu Gln Thr Thr Asp Gly Leu Ala Val Asp Ala Ile Gly Arg
            1125                1130                1135

Lys Val Tyr Trp Thr Asp Thr Gly Thr Asn Arg Ile Glu Val Gly Asn
                1140                1145                1150

Leu Asp Gly Ser Met Arg Lys Val Leu Val Trp Gln Asn Leu Asp Ser
            1155                1160                1165

Pro Arg Ala Ile Val Leu Tyr His Glu Met Gly Phe Met Tyr Trp Thr
    1170                1175                1180

Asp Trp Gly Glu Asn Ala Lys Leu Glu Arg Ser Gly Met Asp Gly Ser
1185                    1190                1195                1200

Asp Arg Ala Val Leu Ile Asn Asn Asn Leu Gly Trp Pro Asn Gly Leu
            1205                1210                1215
```

```
Thr Val Asp Lys Ala Ser Ser Gln Leu Leu Trp Ala Asp Ala His Thr
            1220                1225                1230

Glu Arg Ile Glu Ala Ala Asp Leu Asn Gly Ala Asn Arg His Thr Leu
        1235                1240                1245

Val Ser Pro Val Gln His Pro Tyr Gly Leu Thr Leu Leu Asp Ser Tyr
    1250                1255                1260

Ile Tyr Trp Thr Asp Trp Gln Thr Arg Ser Ile His Arg Ala Asp Lys
1265                1270                1275                1280

Gly Thr Gly Ser Asn Val Ile Leu Val Arg Ser Asn Leu Pro Gly Leu
                1285                1290                1295

Met Asp Met Gln Ala Val Asp Arg Ala Gln Pro Leu Gly Phe Asn Lys
            1300                1305                1310

Cys Gly Ser Arg Asn Gly Gly Cys Ser His Leu Cys Leu Pro Arg Pro
        1315                1320                1325

Ser Gly Phe Ser Cys Ala Cys Pro Thr Gly Ile Gln Leu Lys Gly Asp
    1330                1335                1340

Gly Lys Thr Cys Asp Pro Ser Pro Glu Thr Tyr Leu Leu Phe Ser Ser
1345                1350                1355                1360

Arg Gly Ser Ile Arg Arg Ile Ser Leu Asp Thr Ser Asp His Thr Asp
                1365                1370                1375

Val His Val Pro Val Pro Glu Leu Asn Asn Val Ile Ser Leu Asp Tyr
            1380                1385                1390

Asp Ser Val Asp Gly Lys Val Tyr Tyr Thr Asp Val Phe Leu Asp Val
        1395                1400                1405

Ile Arg Arg Ala Asp Leu Asn Gly Ser Asn Met Glu Thr Val Ile Gly
    1410                1415                1420

Arg Gly Leu Lys Thr Thr Asp Gly Leu Ala Val Asp Trp Val Ala Arg
1425                1430                1435                1440

Asn Leu Tyr Trp Thr Asp Thr Gly Arg Asn Thr Ile Glu Ala Ser Arg
                1445                1450                1455

Leu Asp Gly Ser Cys Arg Lys Val Leu Ile Asn Asn Ser Leu Asp Glu
            1460                1465                1470

Pro Arg Ala Ile Ala Val Phe Pro Arg Lys Gly Tyr Leu Phe Trp Thr
        1475                1480                1485

Asp Trp Gly His Ile Ala Lys Ile Glu Arg Ala Asn Leu Asp Gly Ser
    1490                1495                1500

Glu Arg Lys Val Leu Ile Asn Thr Asp Leu Gly Trp Pro Asn Gly Leu
1505                1510                1515                1520

Thr Leu Asp Tyr Asp Thr Arg Arg Ile Tyr Trp Val Asp Ala His Leu
                1525                1530                1535

Asp Arg Ile Glu Ser Ala Asp Leu Asn Gly Lys Leu Arg Gln Val Leu
            1540                1545                1550

Val Ser His Val Ser His Pro Phe Ala Leu Thr Gln Gln Asp Arg Trp
        1555                1560                1565

Ile Tyr Trp Thr Asp Trp Gln Thr Lys Ser Ile Gln Arg Val Asp Lys
    1570                1575                1580

Tyr Ser Gly Arg Asn Lys Glu Thr Val Leu Ala Asn Val Glu Gly Leu
1585                1590                1595                1600

Met Asp Ile Ile Val Val Ser Pro Gln Arg Gln Thr Gly Thr Asn Ala
                1605                1610                1615

Cys Gly Val Asn Asn Gly Gly Cys Thr His Leu Cys Phe Ala Arg Ala
            1620                1625                1630

Ser Asp Phe Val Cys Ala Cys Pro Asp Glu Pro Asp Ser Arg Pro Cys
```

-continued

```
              1635              1640              1645
Ser Leu Val Pro Gly Leu Val Pro Pro Ala Pro Arg Ala Thr Gly Met
    1650              1655              1660

Ser Glu Lys Ser Pro Val Leu Pro Asn Thr Pro Pro Thr Thr Leu Tyr
1665              1670              1675              1680

Ser Ser Thr Thr Arg Thr Arg Thr Ser Leu Glu Val Glu Gly Arg
                1685              1690              1695

Cys Ser Glu Arg Asp Ala Arg Leu Gly Leu Cys Ala Arg Ser Asn Asp
            1700              1705              1710

Ala Val Pro Ala Ala Pro Gly Glu Gly Leu His Ile Ser Tyr Ala Ile
            1715              1720              1725

Gly Gly Leu Leu Ser Ile Leu Leu Ile Leu Val Val Ile Ala Ala Leu
            1730              1735              1740

Met Leu Tyr Arg His Lys Lys Ser Lys Phe Thr Asp Pro Gly Met Gly
1745              1750              1755              1760

Asn Leu Thr Tyr Ser Asn Pro Ser Tyr Arg Thr Ser Thr Gln Glu Val
                1765              1770              1775

Lys Ile Glu Ala Ile Pro Lys Pro Ala Met Tyr Asn Gln Leu Cys Tyr
            1780              1785              1790

Lys Lys Glu Gly Gly Pro Asp His Asn Tyr Thr Lys Glu Lys Ile Lys
            1795              1800              1805

Ile Val Glu Gly Ile Cys Leu Leu Ser Gly Asp Asp Ala Glu Trp Asp
    1810              1815              1820

Asp Leu Lys Gln Leu Arg Ser Ser Arg Gly Gly Leu Leu Arg Asp His
1825              1830              1835              1840

Val Cys Met Lys Thr Asp Thr Val Ser Ile Gln Ala Ser Ser Gly Ser
                1845              1850              1855

Leu Asp Asp Thr Glu Thr Glu Gln Leu Leu Gln Glu Glu Gln Ser Glu
            1860              1865              1870

Cys Ser Ser Val His Thr Ala Ala Thr Pro Glu Arg Arg Gly Ser Leu
            1875              1880              1885

Pro Asp Thr Gly Trp Lys His Glu Arg Lys Leu Ser Ser Glu Ser Gln
    1890              1895              1900

Val
1905
```